United States Patent [19]

Purdie

[11] Patent Number: 5,593,894
[45] Date of Patent: Jan. 14, 1997

[54] DIRECT CHOLESTEROL ASSAY

[75] Inventor: Neil Purdie, Stillwater, Okla.

[73] Assignee: Research Corporation Technologies, Inc., Tucson, Ariz.

[21] Appl. No.: 468,458

[22] Filed: Jun. 6, 1995

Related U.S. Application Data

[63] Continuation of Ser. No. 91,499, Jul. 14, 1993, abandoned, which is a continuation-in-part of Ser. No. 785,998, Oct. 31, 1991, Pat. No. 5,252,488, which is a continuation-in-part of Ser. No. 639,222, Jan. 9, 1991, Pat. No. 5,246,864, which is a continuation-in-part of Ser. No. 463,473, Jan. 11, 1990, abandoned.

[51] Int. Cl.$^6$ .......................... G01N 33/92; G01N 21/31
[52] U.S. Cl. .............................................. 436/71; 436/171
[58] Field of Search ........................................ 436/71, 171

[56] References Cited

U.S. PATENT DOCUMENTS

| | | | |
|---|---|---|---|
| 3,884,638 | 5/1975 | Dixon et al. | 23/230 B |
| 3,960,493 | 6/1976 | Beitz et al. | 23/231 |
| 4,328,000 | 5/1982 | Horn et al. | 23/230 B |
| 4,360,470 | 11/1982 | Batcho et al. | 260/397.1 |
| 4,486,531 | 12/1984 | Ziegenhorn et al. | 435/19 |
| 4,626,511 | 12/1986 | Artiss et al. | 436/8 |
| 4,701,417 | 10/1987 | Portenhauser et al. | 436/13 |
| 4,814,508 | 3/1989 | Gors et al. | 568/309 |
| 4,883,765 | 11/1989 | Tamir et al. | 436/71 |
| 5,021,197 | 6/1991 | Takeda et al. | 260/399 |
| 5,168,067 | 12/1992 | Miller | 436/71 |
| 5,246,864 | 9/1993 | Purdie | 436/71 |
| 5,252,488 | 10/1993 | Purdie | 436/71 |

FOREIGN PATENT DOCUMENTS

| | | | |
|---|---|---|---|
| WO91/10892 | 7/1991 | WIPO | G01N 21/00 |

OTHER PUBLICATIONS

Perlstein, M. T. et al. "Spectrophotometric study of influences on the direct ferric perchlorate method for the determination of serum cholesterol". Microchem. J., 20(4), 428–439. 1975.

Purdie, et al. (1991) "Direct Measure of the Low–Density Fractions of Serum Cholesterol", Anal. Chem. 63, 2947–2951.

Kholodova, et al. (May 10, 1976) "Chugaev's Reaction for Sterols", Chemical Abstracts 84(19), Abstract No. 132218, 211.

Kholodova (Jun. 13, 1988) "Spectral Properties of Steroid Hormones, Sapogenins and Alkaloids in the Chugaev Reaction as a Function of their Structure", Chemical Abstracts 108(19), Abstract No. 210073, 357.

Feng et al. (1973) "Use of Ferric Ammonium Sulfate in Serum Cholesterol Determination", Clinical Chemistry 19(1), 121–122.

Perlstein, et al. (1975) "Spectrophotometric Study of Influences on the Direct Ferric Perchlorate Method for the Determination of Serum Cholesterol", Micro–chemical Journal 20, 428–429.

Wybenga, et al. (1970) "Direct Manual Determination of Serum Total Cholesterol with a Single Stable Reagent", Clinical Chemistry 16(12), 980–984.

Cox, et al. "The Estimation of Some 17–Alkyl–Substituted Steroids with the Zinc Chloride–Acetyl Chloride (Tshugaev) Reagent and a Postulated Reaction Mechanism", Canadian Journal of Chemisty 39, 217–222.

Grahnen (1974) "A New Method for the Determination of Unconjugated Bilirubin in Human Serum by Spectropolarimetry", Clinica Chimica Acta 52, 187–196.

Ke, et al. (1985) "Versatile Spectrophotometer for Photosynthesis (Light–Induced Changes in Absorbance and Fluorescence Yield, Circular and Linear Dichroism) and Other Biophysical Measurements", Rev. Sci. Instrum. 56, 26–31.

Krivacic, et al. (1971) "A Simultaneous Absorption and Circular Dichroism Data Acquisition System", Analytical Biochemistry 43, 547–555.

Purdie, et al. (1992) "Direct Measure of Total Cholesterol and its Distribution Among Major Serum Lipoproteins", Clinical Chemistry 38, 1645–1646.

Nasipuri, et al. (1979) "Polycyclic Systems. Part 19. Synthesis of 8–Isobutyl–10–Methyl–11H–Indeno[2,1–a]Phenanthrene (Second Diels Hydrocarbon), A Minor Dehydrogenation Product of Cholesterol", J.C.S. Perkin I, 3034–3036.

Purdie, et al. (1989) "Analytical Applications of Polarimetry, Optical Rotatory Dispersion and Circular Dichroism", Analytical Chemistry 61, 77A–89A.

Warnick, et al. (1980) "HDL Cholesterol: Results of Interlaboratory Proficiency Tests", Clinical Chemistry 26, 169–170.

Castelli, et al. (1986) "Incidence of Coronary Heart Disease and Lipoprotein Cholesterol Levels", JAMA 256, 2835–2838.

Superko, et al. (1986) "High Density Lipoprotein Cholesterol Mesurements", JAMA 256, 2714–2717.

Abbott, et al. (1983) "Joint Distribution of Lipoprotein Cholesterol Classes", Arteriosclerosis 3, 260–272.

Grundy, et al. (1989) "The Place of HDL in Cholesterol Management", Arch. Intern. Med. 149, 505–510.

(1988) "Current Status of Blood Cholesterol Measurement in Clinical Laboratories in the United States: A Report from the Laboratory Standardization Panel of the National Cholesterol Education Program", Clin. Chem. 34, 193–201.

Kannel, et al. (1971) "Serum Cholesterol, Lipoproteins, and the Risk of Coronary Heart Disease", Annals of Internal Medicine 74, 1–12.

Primary Examiner—David A. Redding
Attorney, Agent, or Firm—Scully, Scott, Murphy & Presser

[57] ABSTRACT

The present invention relates to the direct quantitative determination of cholesterol and involves the formation of a spectrophotometrically active product of cholesterol obtained by contacting cholesterol with an acyl compound and a perchlorate effective to form the spectrophotometrically active product.

40 Claims, 21 Drawing Sheets

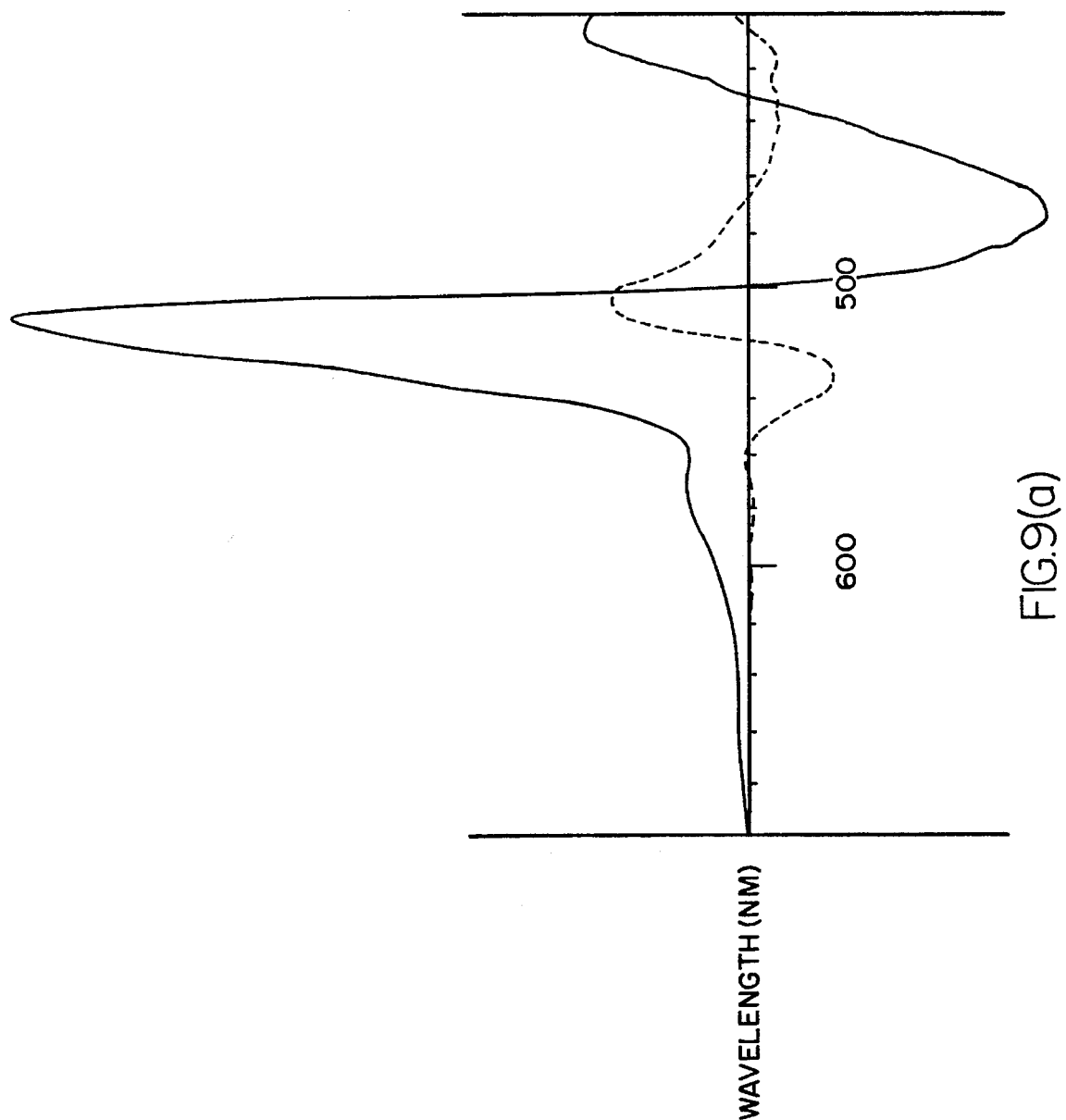

DIRECT CHOLESTEROL ASSAY

The present application is a continuation of U.S. patent application Ser. No. 08/091,499, filed on Jul. 14, 1993, now abandoned which is a continuation-in-part application of U.S. patent application Ser. No. 07/785,998 filed Oct. 31, 1991, now U.S. Pat. No. 5,252,488, which is a continuation-in-part of U.S. patent application Ser. No. 07/639,222, filed on Jan. 9, 1991, now U.S. Pat. No. 5,246,864 which is a continuation-in-part application of U.S. patent application Ser. No. 07/463,473, filed on Jan. 11, 1990 (now abandoned); all of which prior applications are expressly incorporated herein by reference.

FIELD OF THE INVENTION

The present invention is related to a method of forming a spectrophotometrically active cholesterol product that is particularly utile in clinical detection methods for cholesterol using, for example, fluorescence spectrophotometry, derivative absorption spectrophotometry, circular dichroism and more especially absorption spectrophotometry. More specifically, the present invention permits the direct, simultaneous quantitative determination of total cholesterol and cholesterol subfractions in clinical samples. The present invention also relates to a chemical reagent system useful for forming spectrophotometrically active products with analytes such as cholesterol and to a spectrophotometer apparatus useful in the aforesaid absorption detection chemical methods.

BACKGROUND OF THE INVENTION

Although cholesterol levels are widely regarded as a reliable indicator of prospective health problems attributable, for example, to coronary disease, these levels are not easily measured by routine analytical methods involving spectrophotometry since cholesterol is not a colored material. Thus previously known methods for cholesterol determination generally require a color derivatization step. Examples of these include the Liebermann-Burchard reaction, the Zak reaction and the Abell-Kendall reaction, all of which occur in non-aqueous media and require special control of reaction conditions. Another reaction known in this regard is the oxidizing enzyme-dye reaction.

The color derivatization steps known heretofore, however, do not provide a derivative of the cholesterol molecule itself; rather, they provide secondary products of cholesterol oxidation which means that the spectrophotometric measurement of cholesterol is an indirect one. That is, the intensity of the color is not a direct measure of cholesterol concentration.

As noted hereinbefore, most routine analytical methods for practical purposes employ spectrophotometry. Spectrophotometry refers to the measurement of the absorption or transmission of incident light through solutions of test compounds. Typically, compounds of interest have characteristic spectra, transmitting or absorbing specific wavelengths of light, which can be used to determine the presence of these compounds or measure their concentration in test samples. Instruments designed for spectrophotometric absorption have a light source, for which the emitted wavelength is known and may be adjusted, and one or more detectors sensitive to desired wavelengths of transmitted or reflected light. Spectrophotometric absorption can be used to determine the amount of a given compound that is present in a test sample.

Circular dichroism (CD) is a special type of absorption method in which the molecular composition of an analyte results in differential absorption of incident light not only at a specific wavelength but also of a particular polarization state. Circular dichroism is a chiroptical method which allows one to differentiate between different enantiomers; that is, optical isomers having one or more asymmetric carbon atom (chiral) centers. When utilizing CD, generally a sample is illuminated by two circularly polarized beams of light traveling in unison. Both beams pass through the sample simultaneously and are absorbed. If the sample is optically active, the beams are absorbed to different extents. The differences in absorption of the beams can then be displayed as a function of the wavelength of the incident light beam as a CD spectrum. No difference in absorption is observed for optically inactive absorbers so that these compounds are not detected by a CD detecting system. The use of CD as a chiroptical method has been fully described in scientific literature, such as Lambert, J. B. et al. "Organic Structural Analysis", Macmillan, New York, N.Y. 1976.

Early applications of the CD method dealt primarily dealt with elucidation of molecular structures, especially natural products for which a technique capable of confirming or establishing absolute stereochemistry was critical. However, CD has also reportedly been used in a clinical method to quantitatively determine unconjugated bilirubin in blood plasma, Grahnen, A. et al. *Clinica Chimica Acta*, 52, 187–196 (1974). In the method thus disclosed, a complex was formed between bilirubin and human serum albumin as a CD probe for bilirubin analysis.

Clinical applications of circular dichroism are also discussed by Neil Purdie and Kathy A. Swallows in *Analytical Chemistry*, Vol. 61, No. 2, pp. 77A–89A (1989), herein incorporated by reference. Possible clinical applications of CD are disclosed to include measurement of cholesterol levels and detection of anabolic steroids. However, suitable chemical reagents for carrying out such testing are not disclosed.

Regarding the use of spectrophotometric absorption, fluorescence, derivative spectrophotometry or CD methods herein disclosed to measure cholesterol levels, it is noted that the population at large is continually advised that it is prudent to know serum cholesterol levels and constantly reminded that an uncontrolled diet and a lack of exercise can lead to accumulation of arterial plaque that will increase the risk of atherosclerosis and coronary heart disease. Statistical studies, such as those reported by Kannel, W. B. et al. in "Serum Cholesterol, Lipoproteins and the Risk of Coronary Heart Disease: The Framingham Study" *Ann. Intern. Med.*, 74:1–11 (1971) and Castelli, W. P. et al. in "Incidence of Coronary Heart Disease and Lipoprotein Cholesterol Levels", *JAMA*, 256:2835–2838 (1986), have shown that other risk factors, such as age, gender, heredity, tobacco, alcohol consumption etc. must also be considered when counselling patients about the risks.

The magnitude of the program for screening the general public is so immense that automated methods for cholesterol determinations are necessary. The tests currently used differ in complexity from the simple dip-stick approach, which uses a color sensitive reaction on a paper support, to sophisticated lipid profile tests in which the distribution of cholesterol among the various solubilizing molecular species is determined, Abbott, R. D. et al. "Joint Distribution of Lipoprotein Cholesterol Classes, The Framingham Study, *Arteriosclerosis*, 3:260–272 (1983). Here, the dip-stick approach is only a preliminary qualitative test upon which a decision for the fuller, more quantitative measurement can be based.

At the conclusion of a recent extensive study of how health risk factors are related to elevated levels of serum cholesterol, a report entitled "Current Status of Blood Cholesterol Measurement in Clinical Laboratories of the United States, A Report from the Laboratory Standardization Panel of the National Cholesterol Education Program", *Clin. Chem.*, 34:193–201 (1988), was prepared by the Laboratory Standardization Panel (LSP) of the National Cholesterol Education Program (NCEP). In this report, the measure or risk was correlated with three ranges of total cholesterol (TC): low risk if less than 200 mg/dL; moderate risk in the range 200–239 mg/dL; and high risk if greater than 240 mg/dL. In order to place a particular individual into one or another of these categories, all that is required is a serum TC measurement. The other risk factors, such as those identified by Kannel et al. and Castelli et al., supra, are then added as a basis for further patient counselling. This relatively simple approach replaces an earlier recommendation in Kannel et al., supra, and in Superko, H. R. et al. "High-Density Lipoprotein Cholesterol Measurements—A Help or Hinderance in Practical Clinical Medicine", *JAMA* 256:2714–2717 (1986) in which relative risk was established using a ratio of TC to high density lipoprotein cholesterol (HDL-C) equal to 5. A ratio lower than 5 implies a high level of HDL-C and a low relative risk. For this diagnosis, HDL-C is measured in a second independent test.

The same report by the LSP hastened to add that there were serious inaccuracies in measurements made by numerous clinical laboratories in the determination of the amount of TC present in human serum reference standards.

Statistically the results showed that, in data from 1500 laboratories, 47% failed to measure the true value to within a coefficient of variance (CV) of ±5%, and 18% of these failed at a CV of ±10%. As a consequence, the LSP recommended that an improvement in CV to within ±3% for TC should be achieved by 1992. Recent surveys indicate that certified laboratories are well on their way to meeting that challenge, using the current clinical methods and instrumentation, as reported, e.g. in Posnick, L. "Labs now Better at Cholesterol Tests Data Show", *Clin Chem News* 15(9):14 (1989). The LSP did not report the inaccuracies associated with the determination of the distribution of cholesterol among the various lipids and lipoproteins, but did indicate that an evaluation would be made in the future. The very poor proficiency and lack of reliability in the measurement of serum or plasma HDL-C, has been eloquently described in Superko, H. R. et al., supra, and in Warnick, G. R. et al. "HDL Cholesterol: Results of Interlaboratory Proficiency Test" *Clin. Chem.* 26:169–170 (1980) and Grundy, S. M. et al. "The Place of HDL in Cholesterol Management. A Perspective from the National Cholesterol Education Program" *Arch. Inter. Med.* 149:505–510 (1989) where interlaboratory CV's as high as 38% were reported. A 1987 evaluation by the College of American Pathologists (CAP) of the measurement of the same sample for HDL-C by over two thousand laboratories showed that more than one third differed by more than 5% from the reference value. Interlaboratory CV's amount groups using the same method did improve to 16.5%, but it is still too imprecise to be of any predictive clinical value. For this reason, the TC:HDL-C ratio is no longer used in risk assessment, although it offers potential advantages in defining the true clinical picture.

Regarding presently used lipid profile studies, cholesterol is known to be distributed in the serum mainly associated with high density lipoprotein (HDL-C) and low density lipoprotein (LDL-C) fractions and with triglycerides as the very low density lipoprotein cholesterol (VLDL-C) fraction. There is plenty of statistical evidence from a number of long term clinical tests to indicate that a high proportion of HDL-C and a low proportion of LDL-C is associated with lower relative risk or in simpler terms, high levels of LDL-C are to be avoided where possible. HDL-C is beneficial, provided the level is not excessively low, i.e., less than 30 mg/dL. VLDL-C cholesterol has not been implicated in any risk determination, but high triglyceride itself can be a serious problem.

In a typical lipid profile study, total cholesterols are measured directly and HDL-C is measured in the supernatant remaining after treatment of the sample with an agent to precipitate out LDL-C and VLDL-C. VLDL-C is taken to be a fixed fraction (e.g., 0.2) of the triglyceride, which is also measured directly in a separate assay. LDL-C is calculated from these figures and is not measured directly. The propagation of errors in each of the three independent measurements make LDL-C the fraction known with least overall accuracy and precision, although it may be the most significant aspect of cardiovascular risk. Because of this, it is difficult to meaningfully monitor and establish that clinical progress has been made in LDL-C reduction therapy with time.

At a workshop and subsequent roundtable session held at the 43rd Meeting of the American Association for Clinical Chemistry, the present state of the art in this area was summarized, as reported in Baillie, E. G. et al. "Standardization and Clinical Utility of Lipid Determinations", Workshop, 43rd National Meeting American Association for Clinical Chemistry, 1991 and Warnick, G. R. "Standardization of HDL Cholesterol Measurement" Roundtable, 43rd National Meeting, American Association for Clinical Chemistry, 1991. From these proceedings, it was concluded that accuracy is essential in HDL-C measurement. While presently available precipitation methods can give satisfactory results, the values obtained by these methods in routine clinical laboratory settings do not meet real medical needs. The CAP comprehensive chemistry proficiency survey from 1982 to 1991 for HDL-C showed interlaboratory CVs of about 20% in 1991, with no overall improvement since 1982. The CVs delivered by clinical instruments used for HDL-C measurements ranged from 7.6% for the DIMENSION to 50% for the EKTACHEM.

At the sessions, it was also noted that direct methods for LDL cholesterol are needed. The use of triglyceride determinations to estimate VLDL-C by the Friedewald equation is, at present, the method of choice. To quote the workshop syllabus, "The variability typically observed in the measurement of total and HDL cholesterol and triglycerides may preclude attaining acceptable precision. In fact, to achieve the ideal precision in LDL cholesterol estimation, the precision of the constituent measurements must be better than their ideal specifications."

It is thus established that there is a need for a relatively simple, reliable and repeatable assay method to directly and simultaneously determine the amount of cholesterol, both total cholesterol and its distribution among the various subfractions without the need for precipitation or separate measurements of these subfractions.

SUMMARY OF THE INVENTION

The present invention provides a method of forming a spectrophotometrically active cholesterol product which can be employed in an assay for the direct, simultaneous, quantitative determination of total cholesterol and its distribution among HDL-C, LDL-C and VLDL-C subfractions. The spectrophotometric activity of the product may be measured by conventional absorption, fluorescence, first and second derivative spectrophotometrics, as well as circular dichroism.

Thus, in one embodiment the present invention provides a method for forming a spectrophotometrically active product of cholesterol which comprises contacting cholesterol with an acyl compound and a perchlorate effective to form a spectrophotometrically active product with the cholesterol. When formed in a test sample, for example, the spectrophotometric activity may be evaluated to determine the amount of cholesterol present in the sample, including its distribution among HDL-C, LDL-C and VLDL-C subfractions. The method of this embodiment permits a quick and repeatable method for the direct, simultaneous quantitative determination of cholesterol, both total cholesterol and subfraction distribution, at ambient temperature, without the need for precipitation or separate subfraction measurement.

In another embodiment the present invention provides for a clinical method for determining the amount of cholesterol (in cholesterol subfractions) in a test sample, by forming a reaction product with the cholesterol and then either performing step ($a^1$), ($a^2$), ($a^3$) or ($a^4$), wherein steps ($a^3$) and ($a^4$) may be followed by calculation of cholesterol concentrations using matrix mathematics and constants derived for the particular cholesterol subfraction analyzed:

Step ($a^1$) determining the CD absorption spectrum of the test sample over a range from about 150 to 700 nm (preferably from about 360 nm to 700 nm);

Step ($a^2$) determining the CD absorption of the test sample at one or more discrete wavelengths within a range from about 150 nm to 700 nm (preferably from about 360 nm to 700 nm);

Step ($a^3$) determining the spectrophotometric, fluorescence or derivative spectrophotometric absorption of the test sample at three or more discrete wavelengths within a range from about 150 nm to 700 nm (preferably about 360 nm to 700 nm).

Step ($a^4$) determining the spectrophotometric fluorescence or derivative spectrophotometric absorption of the test sample over a range from about 150 nm to 700 nm (preferably from about 360 nm to 700 nm).

The invention further provides novel absorption detection apparatuses for practicing certain of the present inventive methods, which apparatuses are exemplified, but not limited, by the following:

A spectrophotometric absorption instrument for determining the amount of VLDL-C, LDL-C, HDL-C and TC present in a test sample, the instrument comprising means for determining the spectrophotometric absorption spectrum of the test sample at 3 or more distinct wavelengths, within the range of about 150 to 700 nm (preferably 360 nm–700 nm), and means for determining the amount of VLDL-C, LDL-C, HDL-C and TC present in the test sample based on, for example, the spectrophotometric absorption of the cholesterol reaction products in the test sample. Optionally, the instrument further comprises means for adding reagent to the test sample.

BRIEF DESCRIPTION OF THE DRAWINGS

The present invention will become more fully understood from the detailed description given here and below and the accompanying drawings which are given by way of illustration only, and thus, are not limitative of the present invention.

FIG. 5 is a schematic of a CD, wherein:

LS is the high intensity conventional light source or laser source; M1 and M2 are monochromators required for full spectral data; P is the linearly polarizing element; Q is the circularly polarizing element; S is the sample cell; D is the detector (of which there may be up to three); and REC is the recorder.

Figure 6:
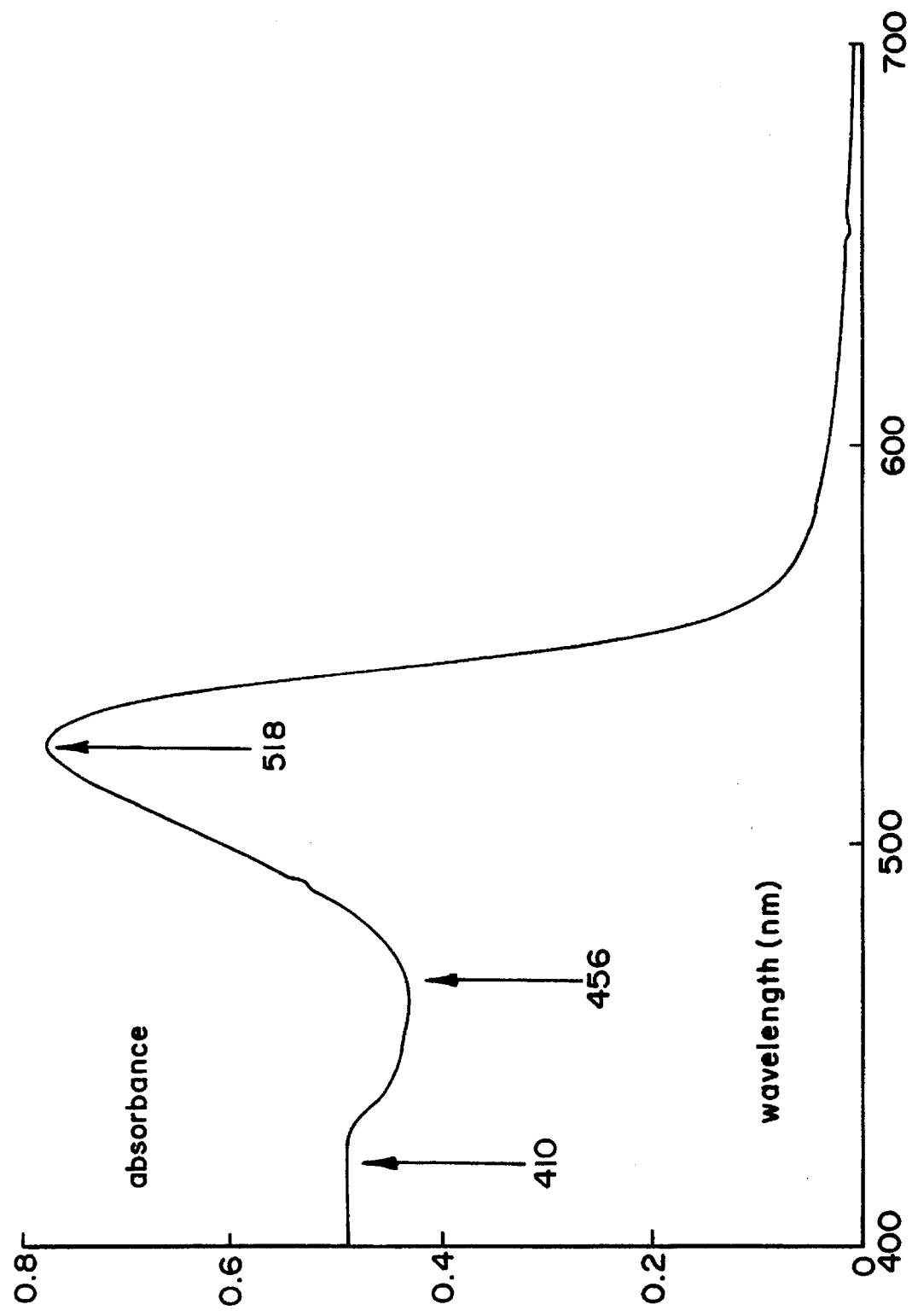

FIG. 6 is a graph of the absorption spectrum of whole serum over the wavelength range of 400 nm–700 nm.

Figure 7A:
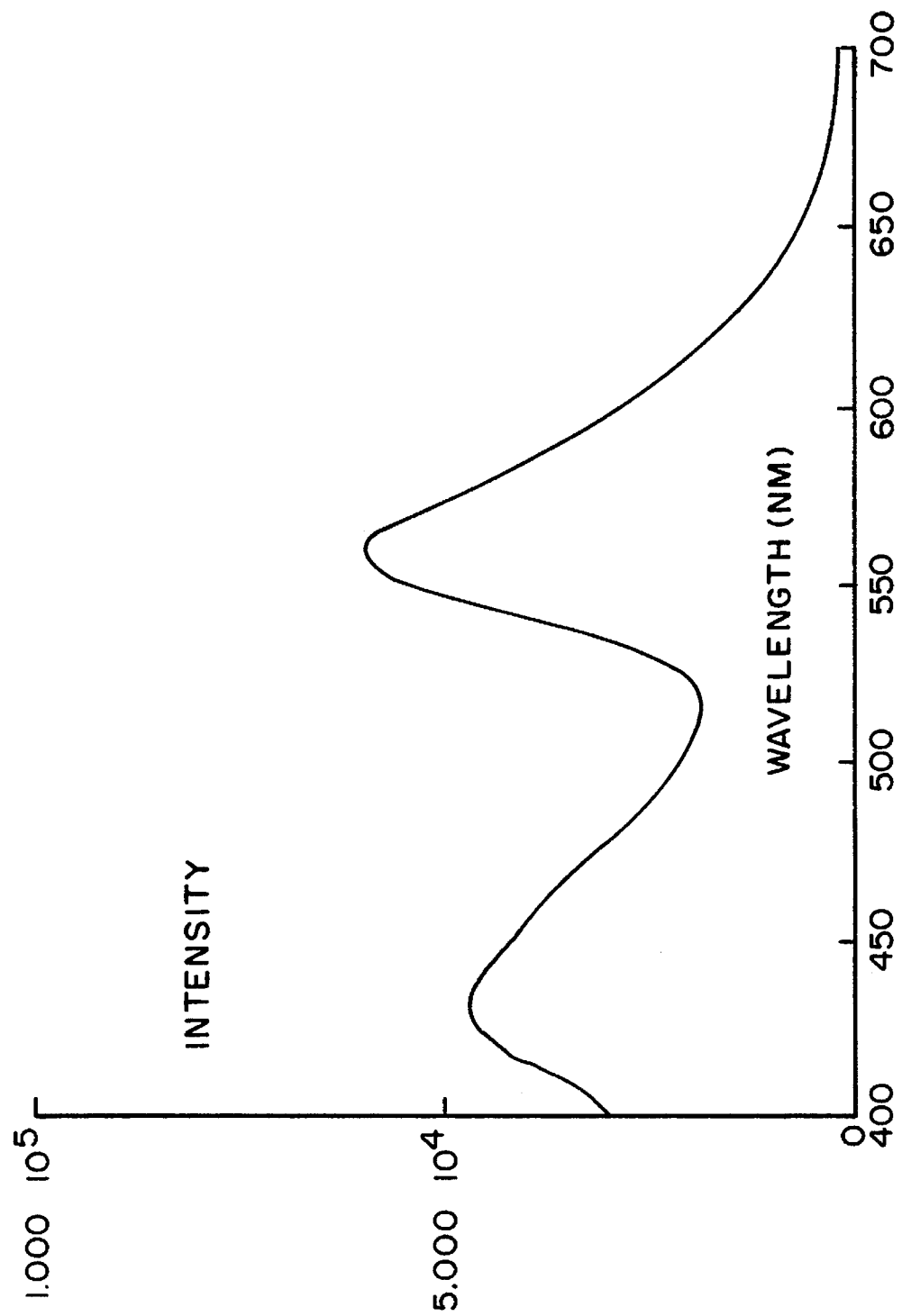
Figure 7B:
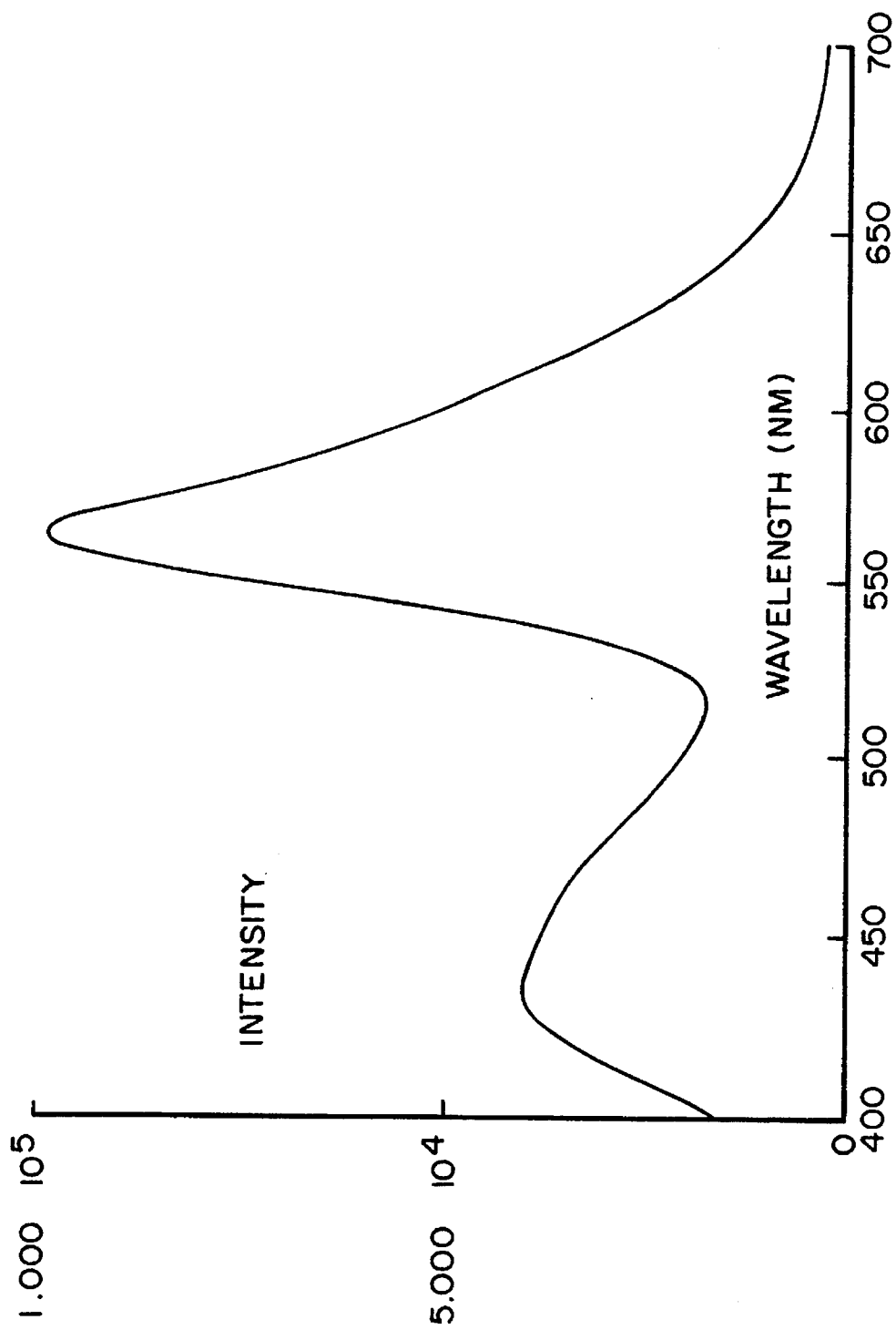
Figure 7C:
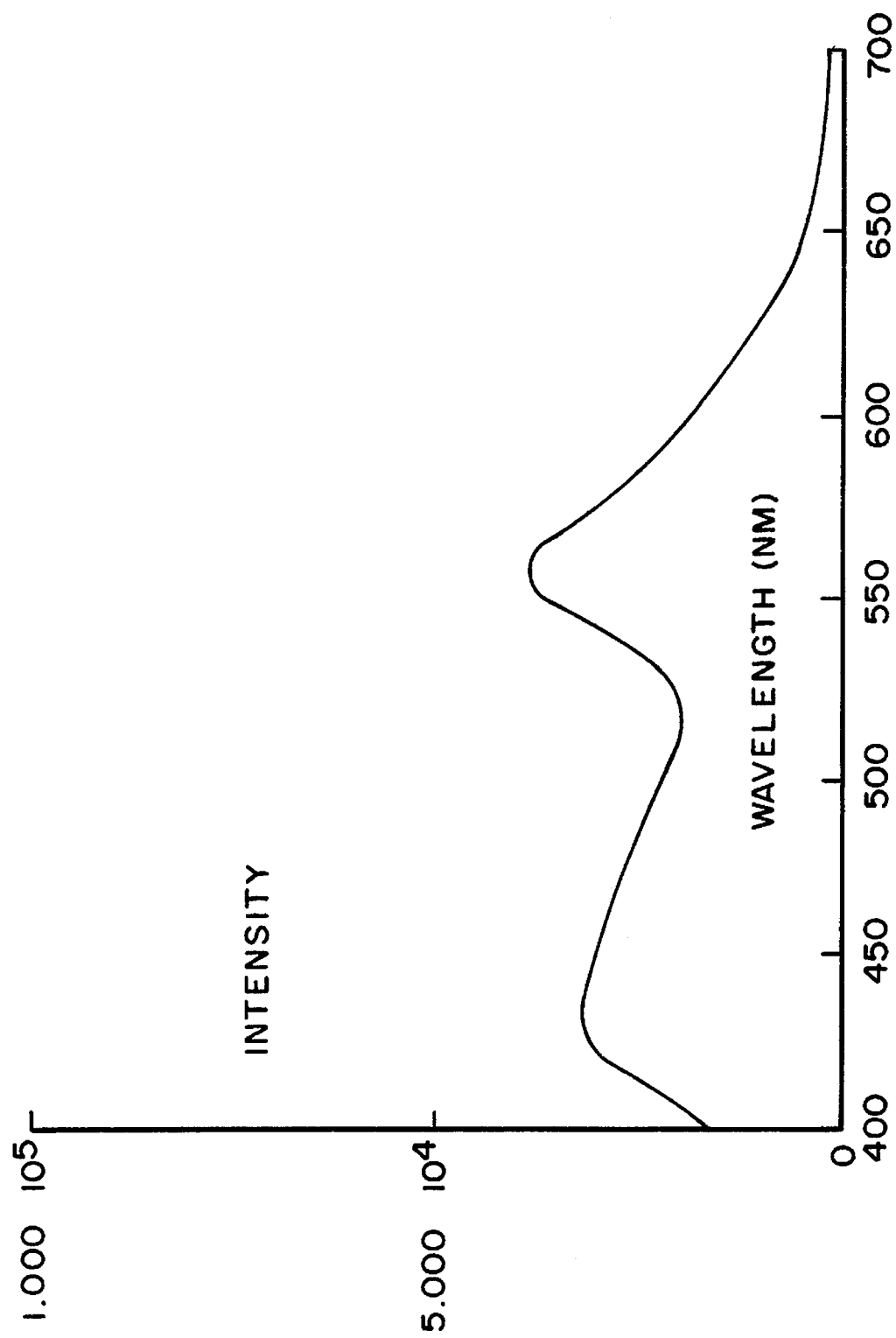
Figure 8A:
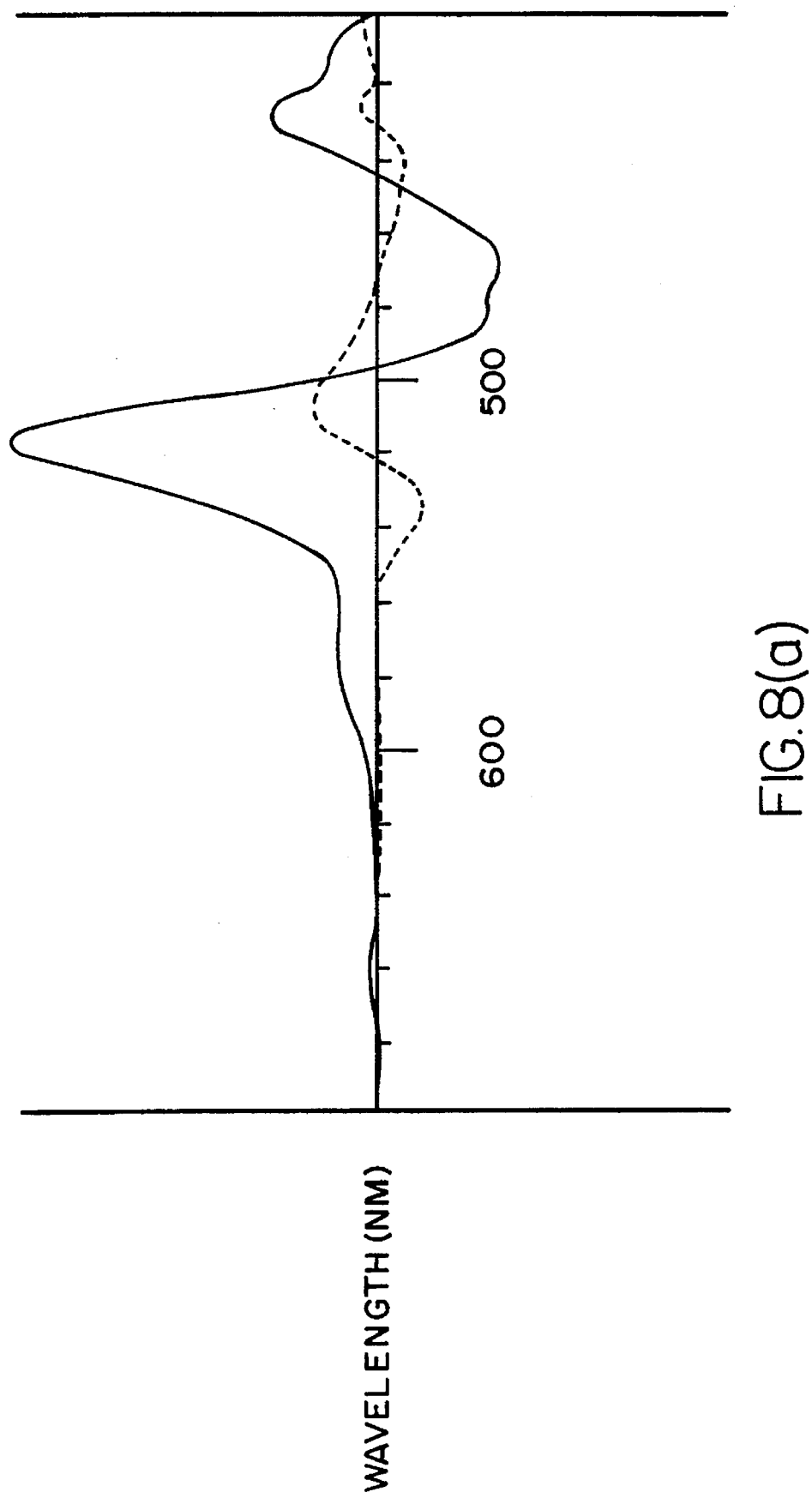
Figure 8B:
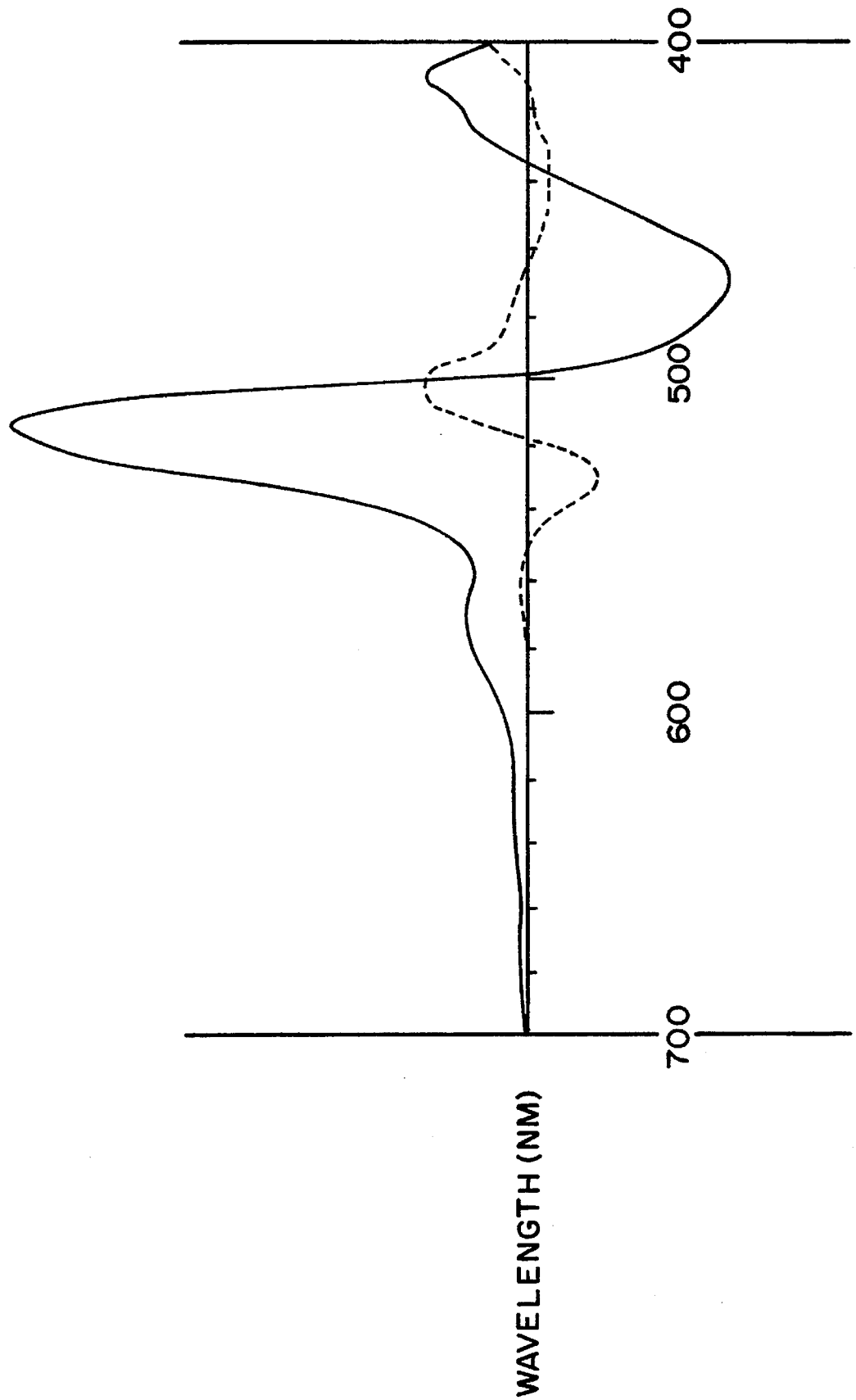
Figure 8C:
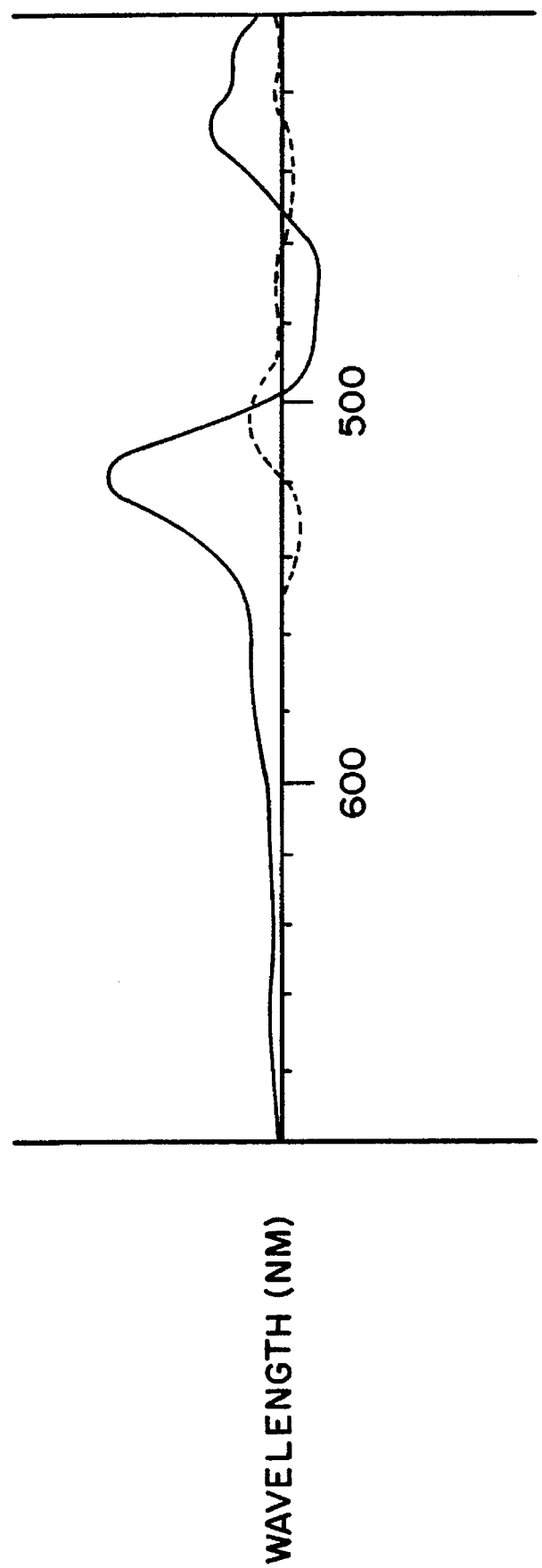
Figure 9B:
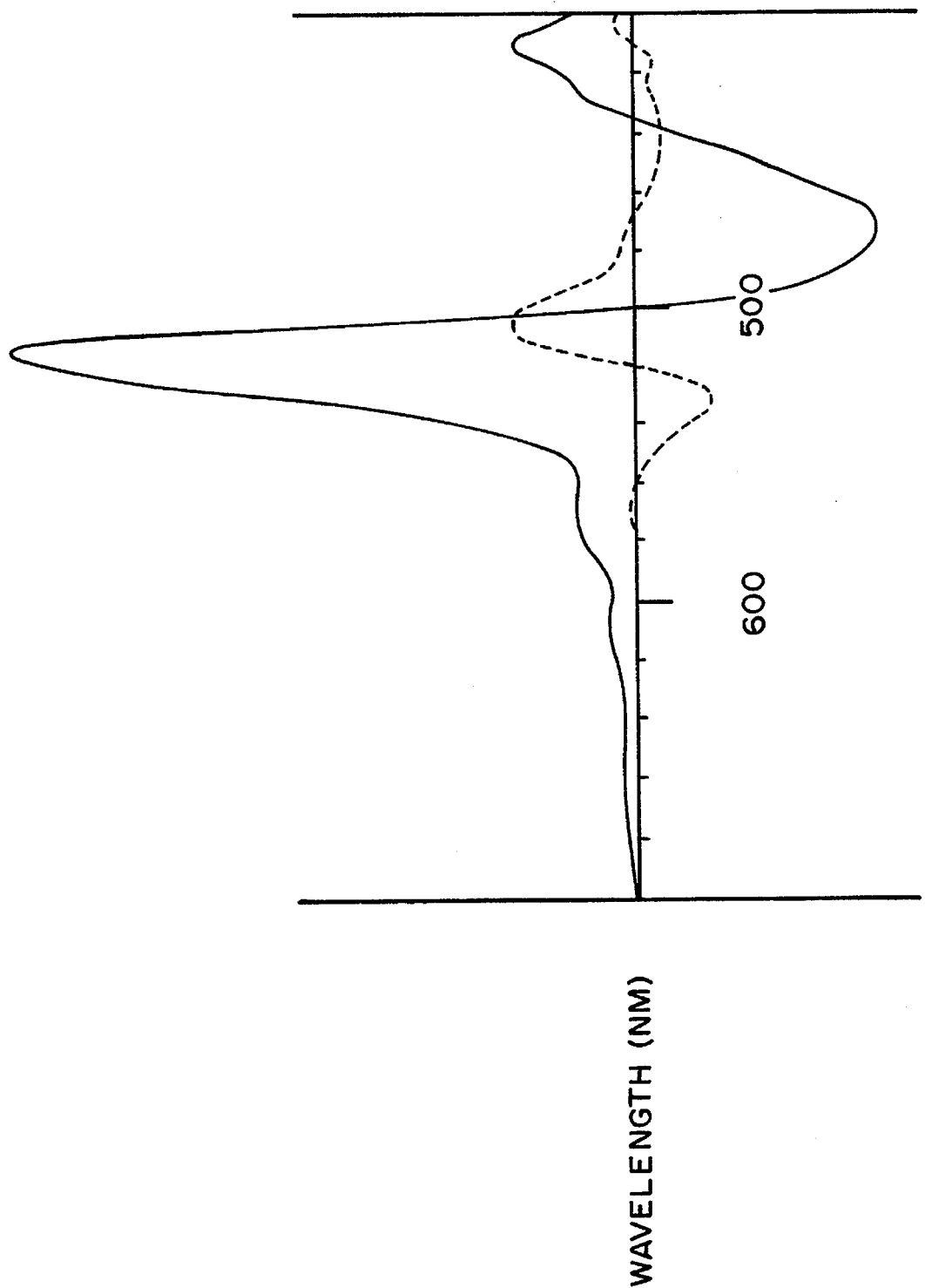

FIG. 7(a) is a graph of the fluorescence spectrum for VLDC-C subfraction;

FIG. 7(b) is a graph of the fluorescence spectrum for LDL-C subfraction;

FIG. 7(c) is a graph of the fluorescence spectrum of HDL-C subfraction;

FIG. 8(a) is a graph of the first (solid line) and second (dotted line) derivative of the conventional absorbance spectrum of the VLDL-C subfraction (sigma);

FIG. 8(b) is a graph of the first (solid line) and second (dotted line) derivatives of the conventional absorbance spectrum of the LDL-C subfraction (sigma);

FIG. 8(c) is a graph of the first (solid line) and second (dotted line) derivatives of the conventional absorbance spectrum of the HDL-C subfraction (sigma);

FIG. 9(a) is a graph of the first (solid line) and second (dotted line) derivatives of the Serum A test sample; and FIG. 9(b) is a graph of the first (solid line) and second (dotted line) derivatives of a Serum B test sample.

Figure 10:
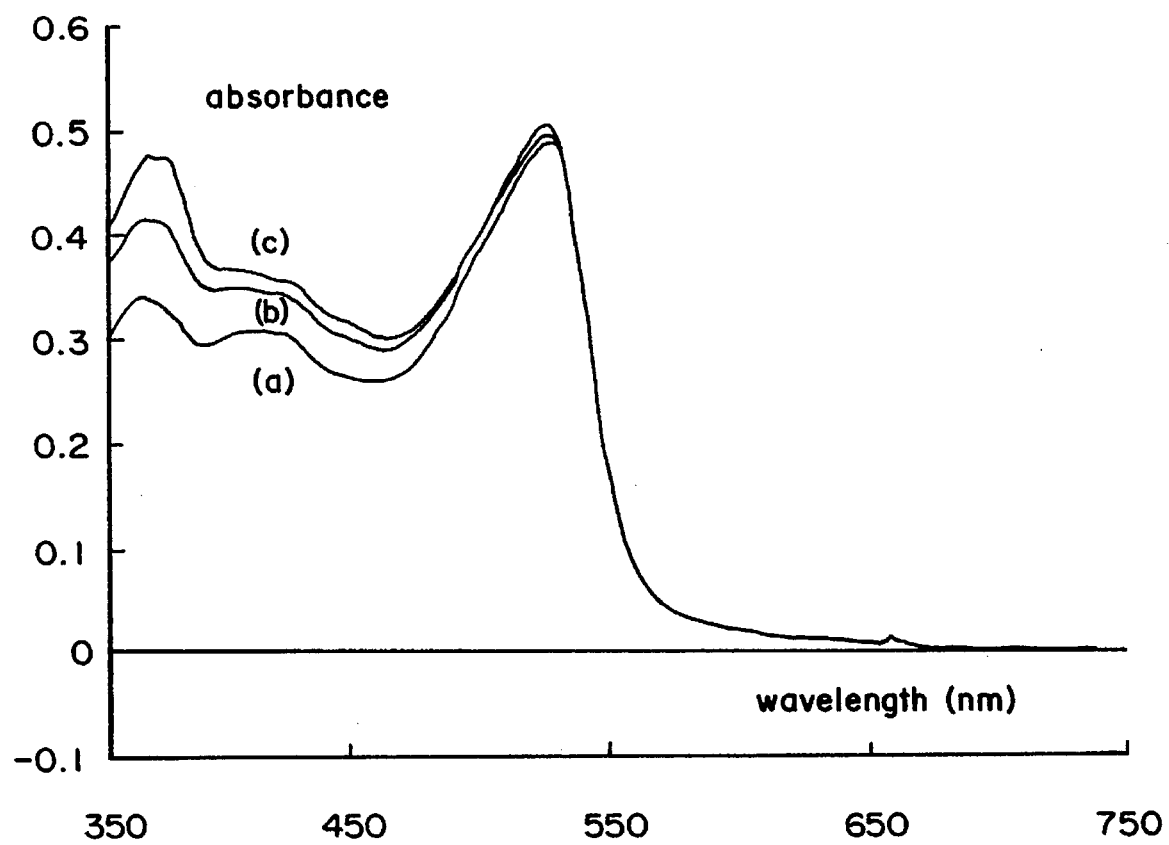

FIG. 10 is a graph of the absorbance spectra for three samples wherein total cholesterol for each sample was similar but triglyceride (TG) levels varied from about 30 mg/dL (Curve a), about 306 md/dL (Curve b) and about 630 mg/dL (Curve c).

Figure 11A:
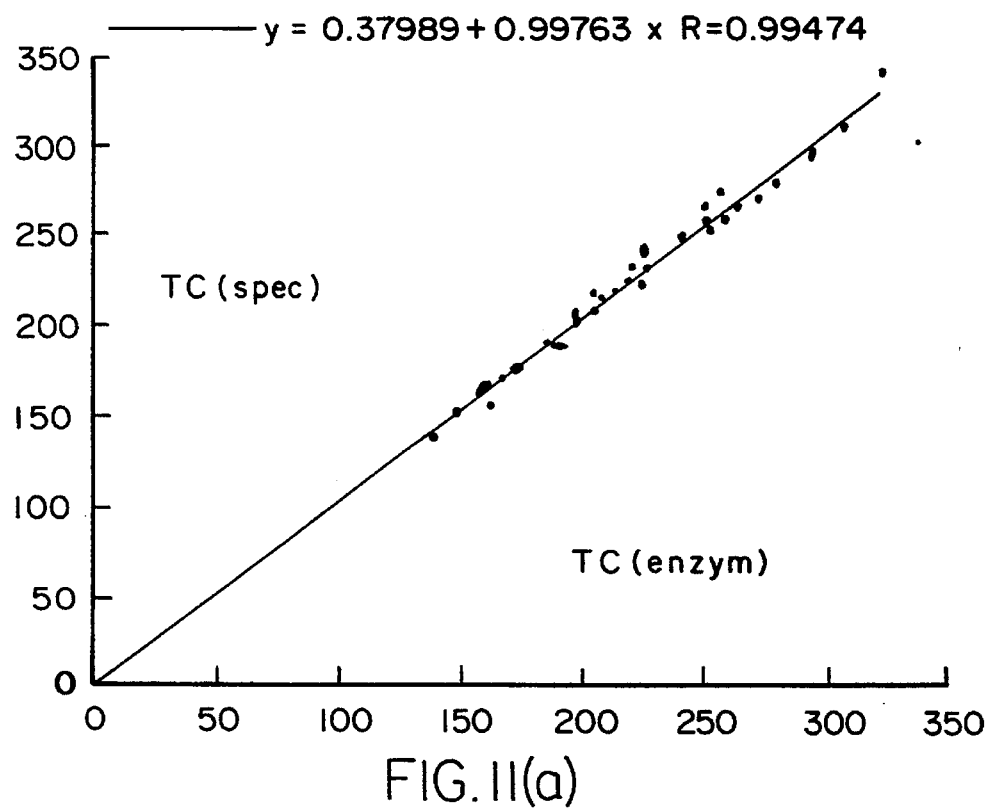
Figure 11B:
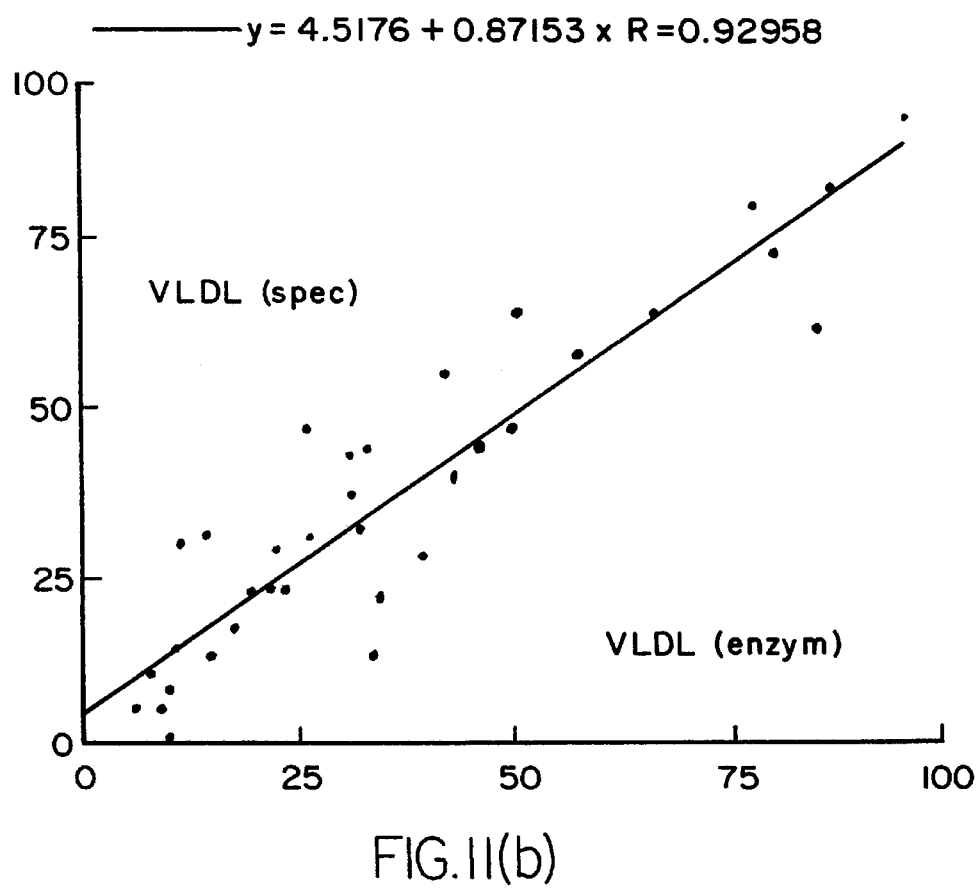
Figure 11C:
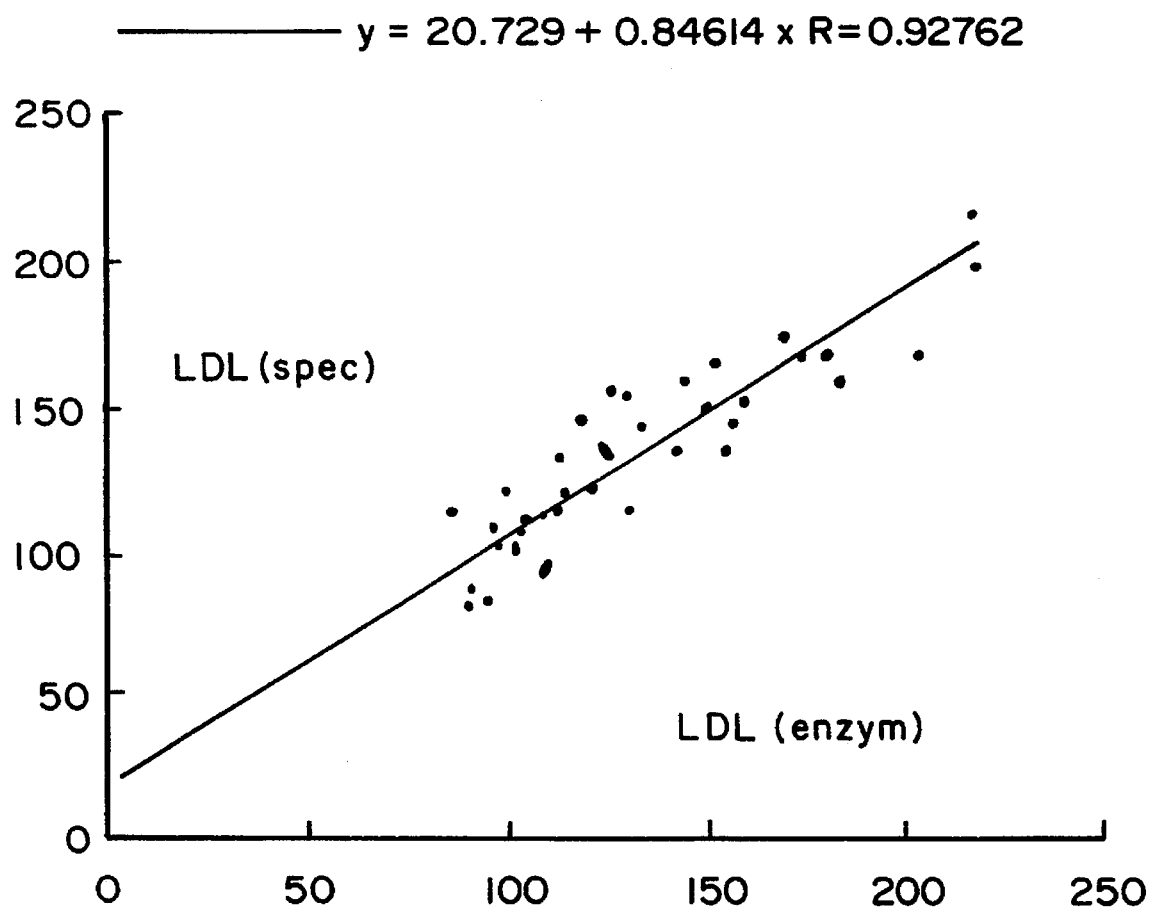

FIGS. 11a, 11b and 11c are graphs respectively depicting the correlation between total cholesterol (TC), VLDL-C and LDL-C in 35 test samples as measured by the spectrophotometric active product in accordance with the present invention (denoted as "spec") and as measured by a commercially available technique (denoted "enzym").

Figure 12A:
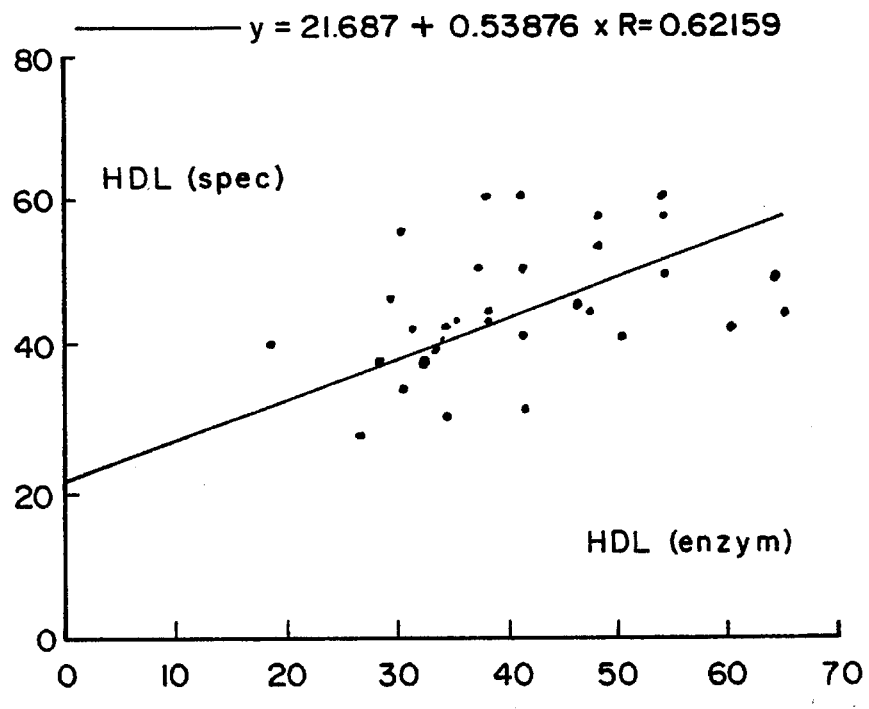
Figure 12B:
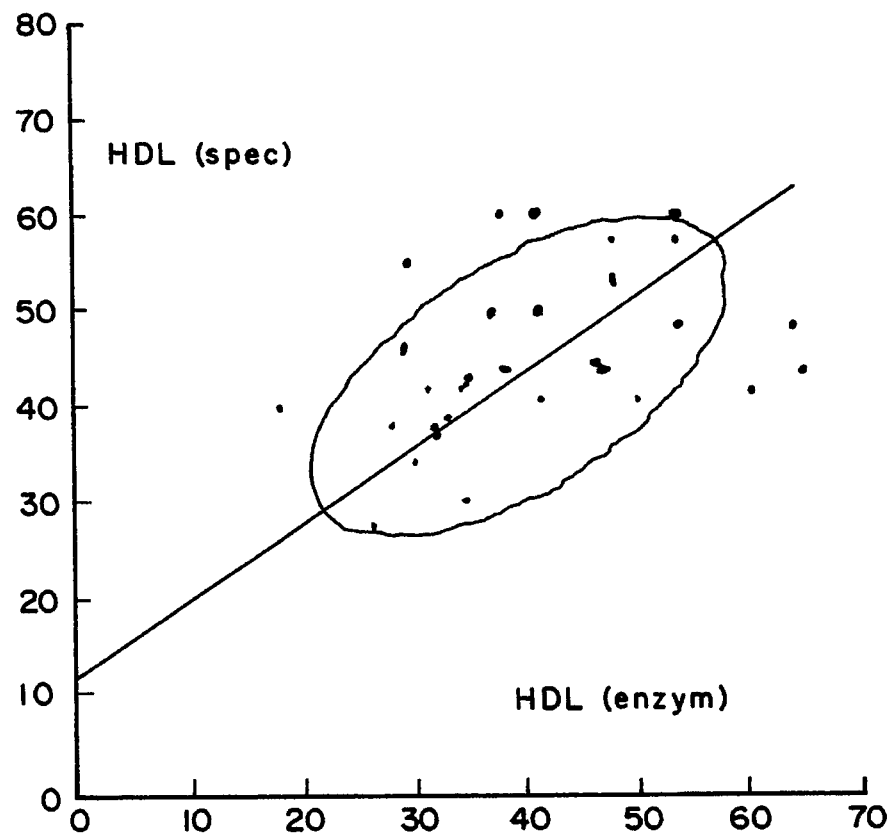

FIGS. 12a and 12b are graphs depicting the correlation between HDL in 35 test samples as measured by the spectrophotometrically active product in accordance with the present invention (denoted as "spec") and as measured by a commercially available technique (denoted as "enzym").

Figure 13A:
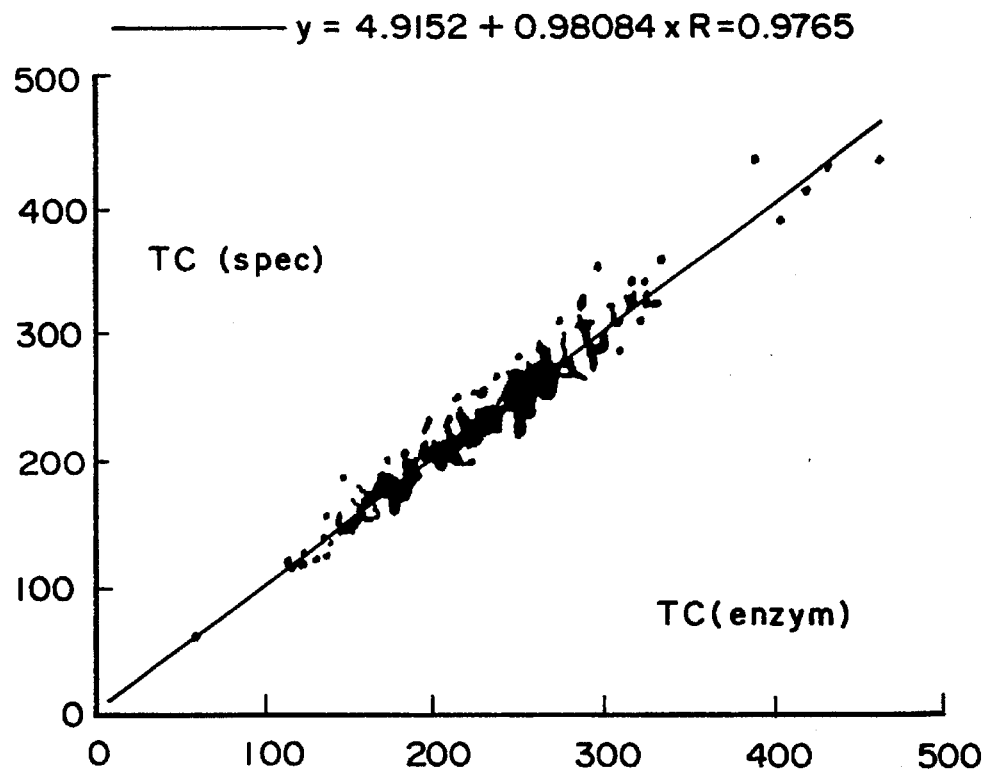
Figure 13B:
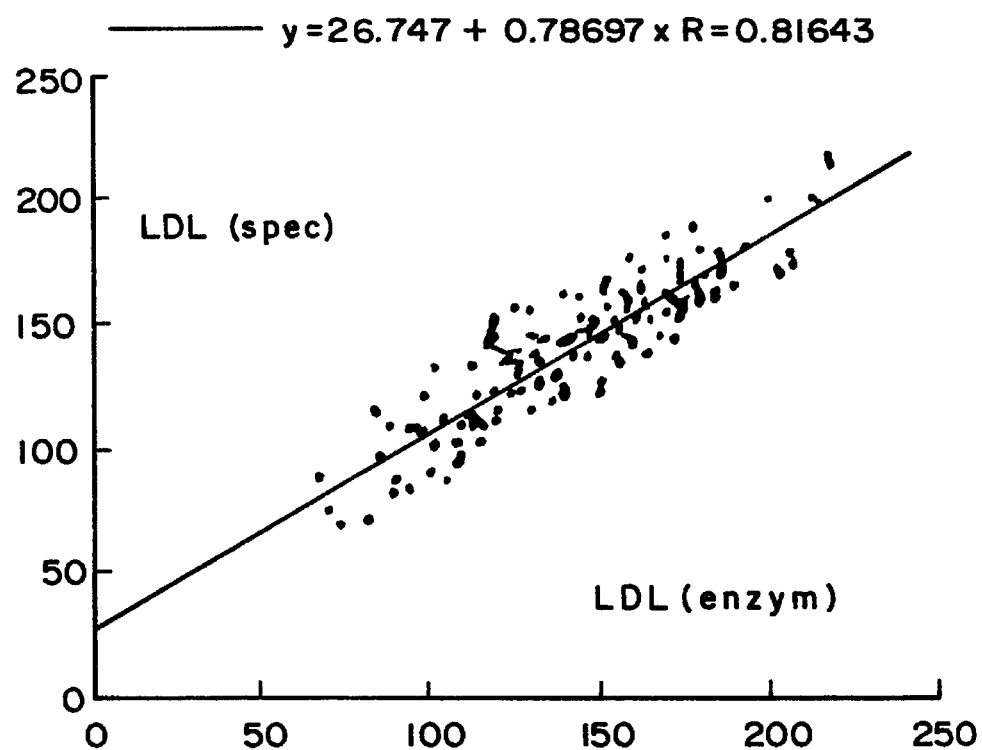
Figure 13C:
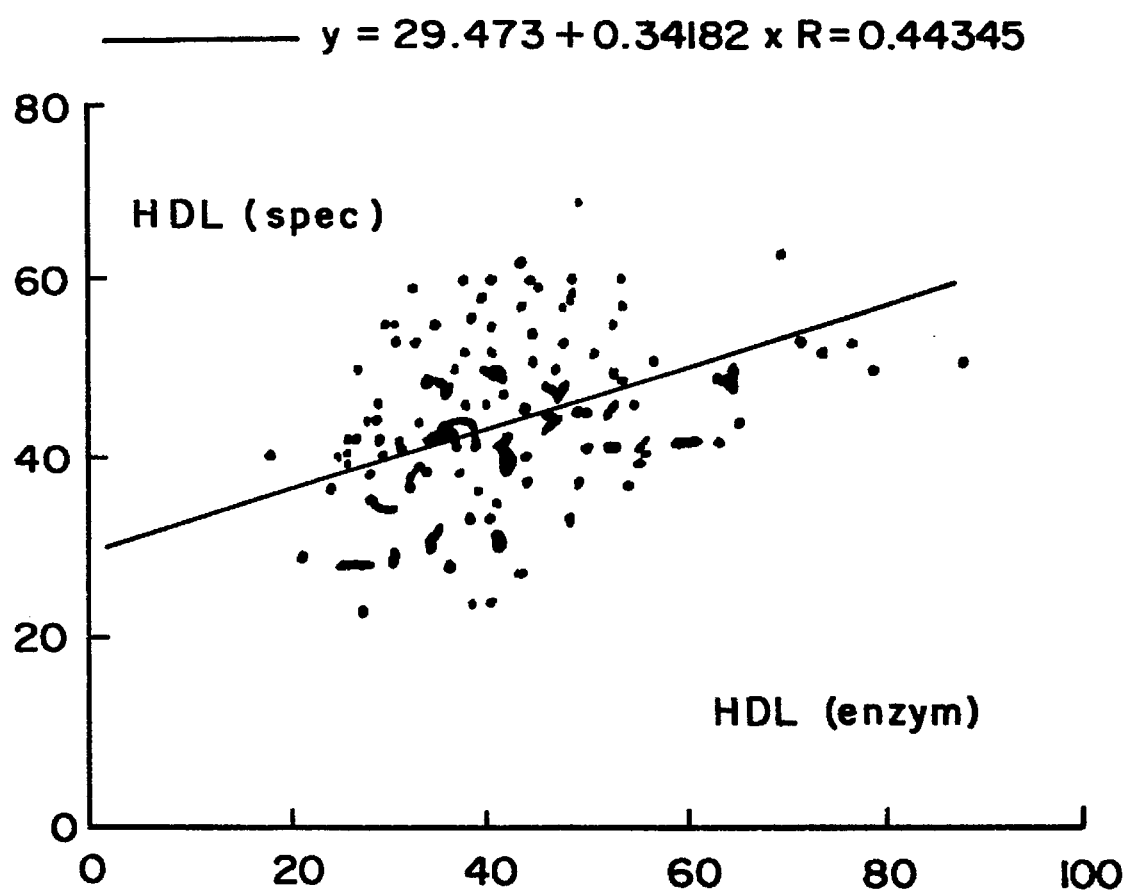

FIGS. 13a, 13b and 13c are graphs depicting the correlation between TC, LDL and HDL in several hundred samples as measured by the spectrophotometrically active product in accordance with the present invention (denoted as "spec") and as measured by a commercially available technique (denoted as "enzym").

Figure 14A:
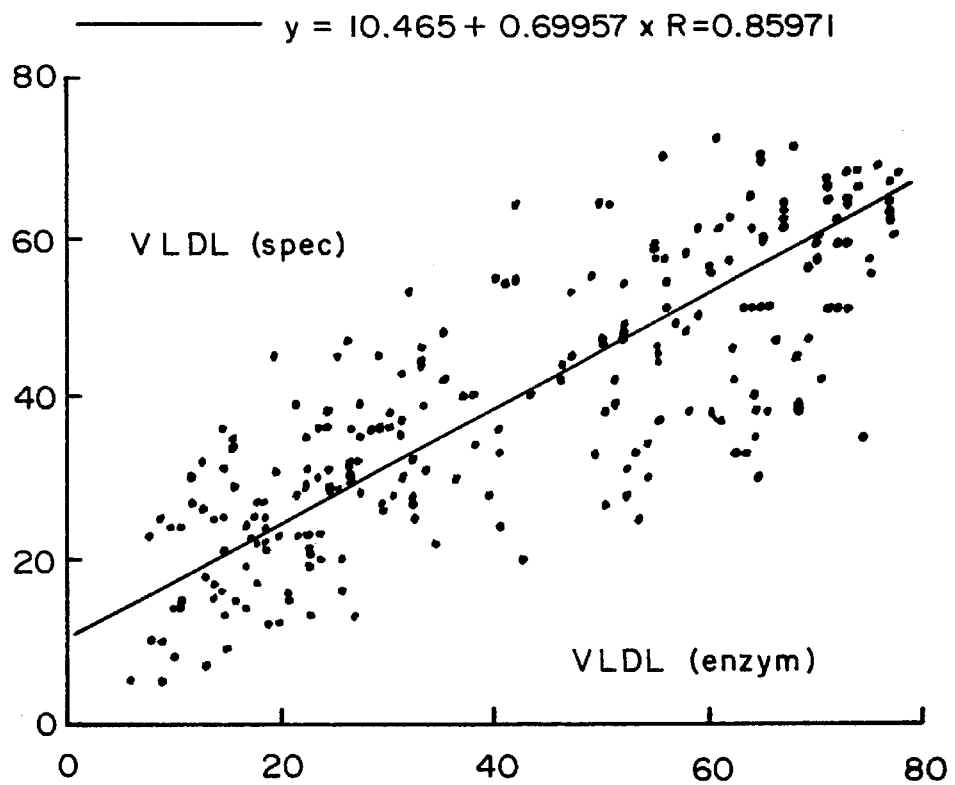
Figure 14B:
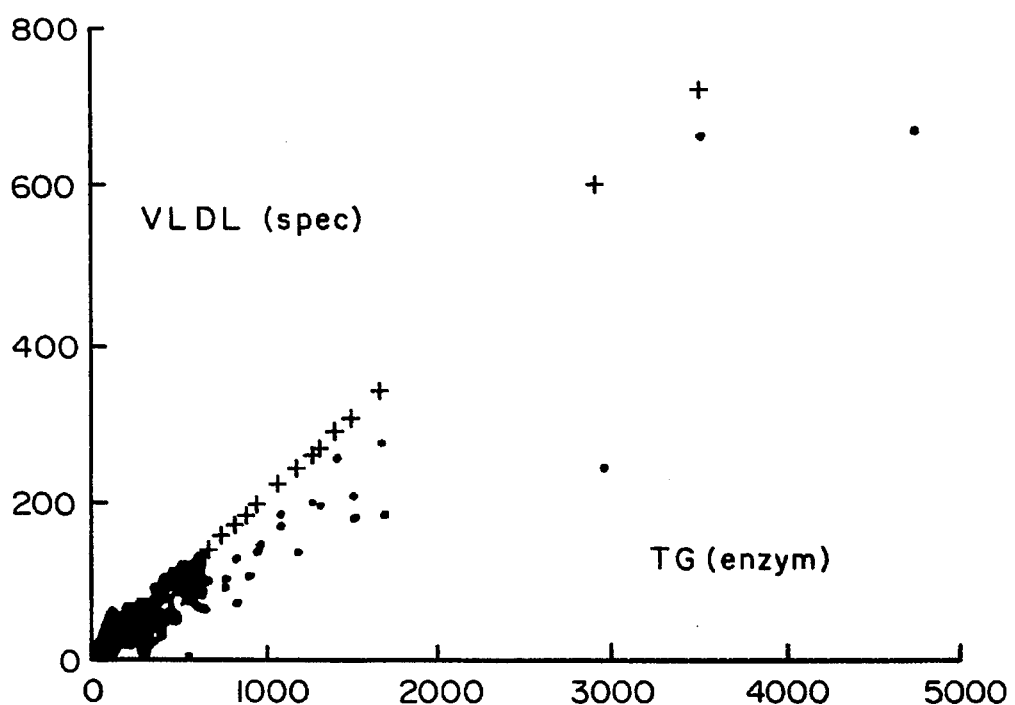

FIGS. 14a and 14b are graphs depicting the correlation between VLDL as measured by the spectrophotometrically active product in accordance with the present invention (denoted as "spec") and as measured by a commercially available technique (denoted as "enzym") wherein the samples had TG<400 mg/dL (FIG. 14a) and wherein TG was between 400 and 1000 mg/dL (FIG. 14b).

Figure 15A:
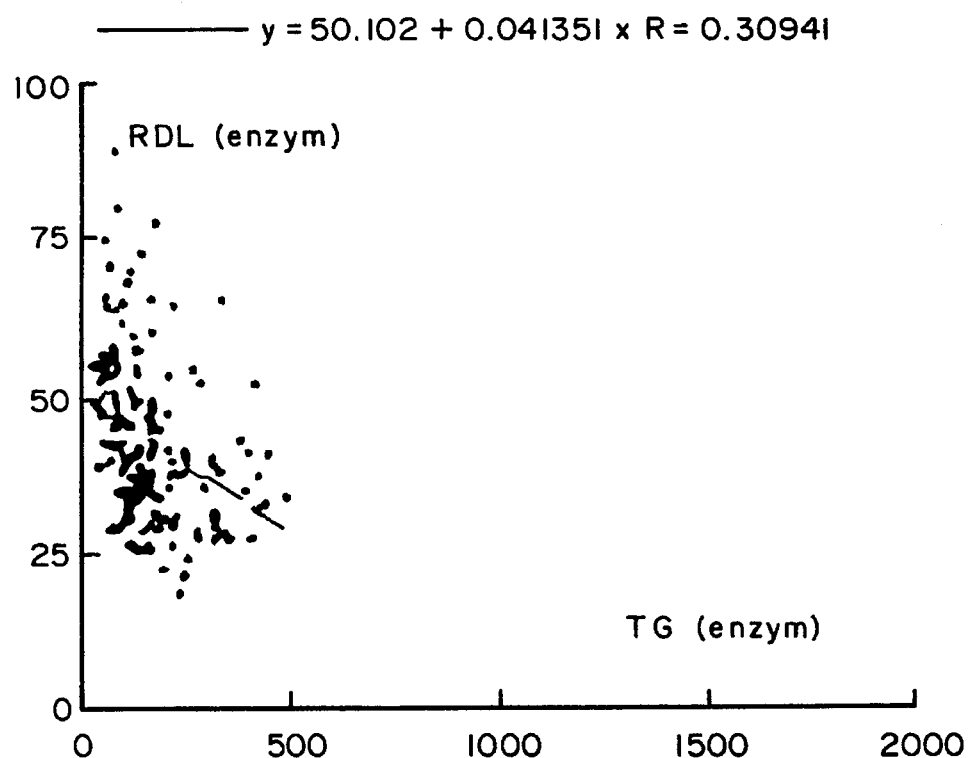
Figure 15B:
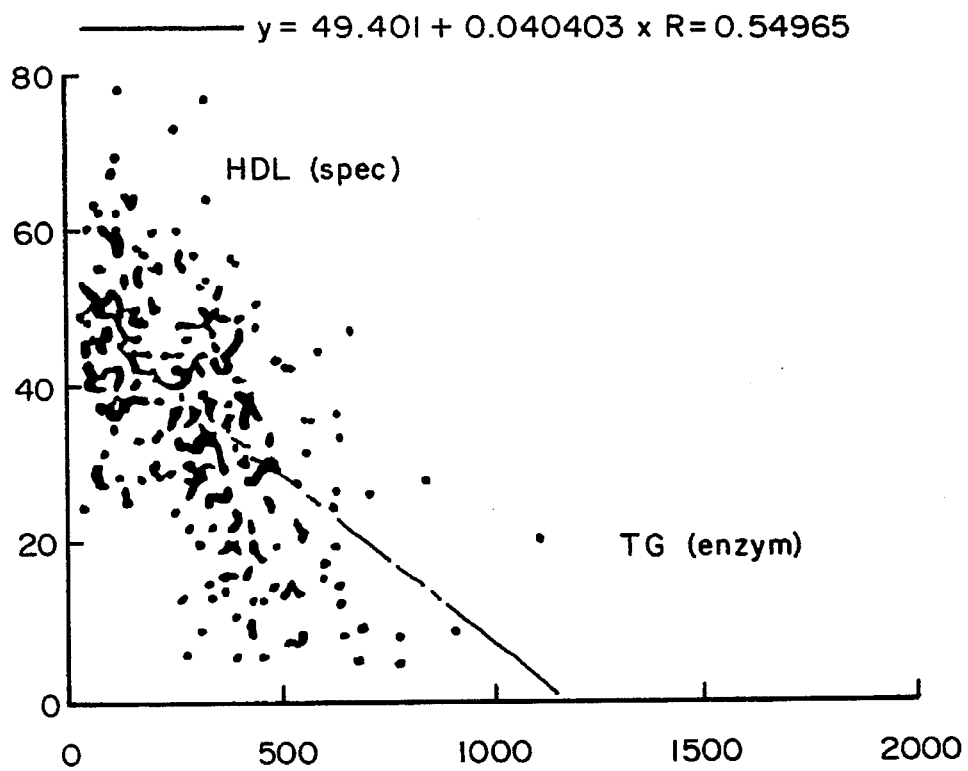

FIGS. 15a and 15b are graphs depicting the inverse correlation between HDL and TG as measured by a commercially available technique (denoted as "enzym") (FIG. 15a) and as measured by the spectrophotometrically active product in accordance with the present invention (denoted as "spec") (FIG. 15b).

DETAILED DESCRIPTION OF THE INVENTION

The following detailed description of the present invention is provided as an aid in the practice of the present invention. Much of the discussion appearing herein relates to methods and instruments for determining TC and the amount of cholesterol subfractions present in a test sample, however, the present invention should not be considered to be unduly limited by such discussions. This is true, since those skilled in the art will generally understand that the reagents, reagent ratios, reaction conditions and apparatuses herein disclosed may be modified without departing from the spirit or scope of the present invention.

The following discussion first provides a glossary of certain terms used herein, and then considers the inventive methods herein disclosed and concludes with a discussion of novel apparatus, which are particularly useful in performing the methods herein disclosed.

The following Glossary of Terms is provided to remove any ambiguity, which may exist as to the use of certain terms and abbreviations used herein.

Figure 5:
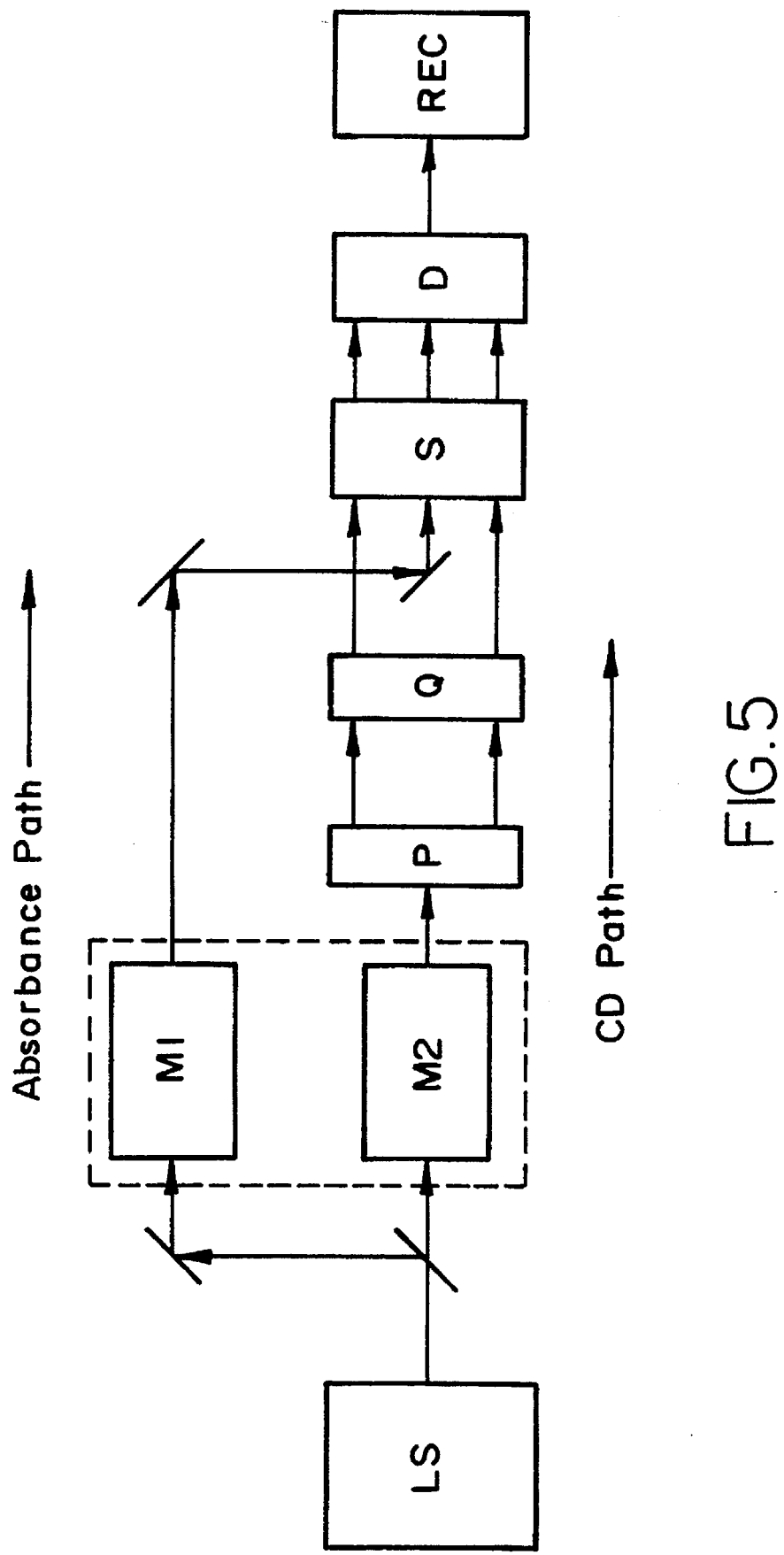

The term "CD instrument" as used herein, means a Circular Dichroism Instrument. Such instruments are available commercially or may be constructed from parts, which may be commercially available. Additionally, FIG. 5 is included herewith to provide a simple schematic of how a CD works. As can be seen in FIG. 5, light from a light source (LS) is linearly polarized with linear polarizers (P) and then circularly polarized in opposite directions by circular polarizers (Q) and then shown through a specimen cell (S), whereupon absorbance is measured by a detector (D), the difference in absorption of the oppositely polarized light beams is measured and plotted as a function of wavelength to produce a CD spectrum, or alternatively, may be recorded at preselected wavelengths.

The term "LDL cholesterol" (abbreviated LDL-C) as used herein, means low density lipoprotein cholesterol. The term "HDL cholesterol" (abbreviated HDL-C) as used herein, means high density lipoprotein cholesterol. The term "VLDL cholesterol" (abbreviated VLDL-C) as used herein, means very low density lipoprotein cholesterol, the abbreviation "(VLDL+LDL)-C" as used herein means the combined VLDL-C and LDL-C fractions and the term "total cholesterol" (abbreviated TC) as used herein, means the sum of the cholesterol subfractions in a test sample, i.e., TC=HDL-C+LDL-C+VLDL-C. The term "cholesterol subfraction" as used herein, refers to any or all of the HDL-C, LDL-C and VLDL-C.

The term "Chugaev reagent" as used herein, means a reagent described by Cox and Spencer in *Can. J. Chem.*, 29, 217 (1951) or to reagents derived from that basic reagent configuration by varying the proportions of the acetyl chloride, zinc chloride and acetic acid, or by substituting zinc acetate in acetyl chloride for zinc chloride/acetic acid.

The term "Chugaev reaction product" as used herein, means any of the reaction product(s) of cholesterol with Chugaev reagents. A "Chugaev reaction" utilized herein to form a Chugaev reaction product of the present invention, is discussed in the above-mentioned literature of Coy and Spencer and is thought to involve dehydration and opening of the B-ring of the steroid to form an optically active colored reaction product.

The term "test sample", "clinical test sample" or "serum test sample" as used herein, refers to a whole blood test sample or a whole blood test sample having the cell bodies removed therefrom by means which are well known to those skilled in the art (e.g., by centrifugal force, a filtering mechanism or the like).

The term "spectrophotometric absorption" as used herein refers to measurement of the absorption (or, conversely, transmission) of incident light by colored compounds at specific wavelengths, irrespective of the state of polarization of the light.

The term "spectrophotometric absorption detection" as used herein means detection and quantitation of analytes in a test sample by measuring their absorption of light at various wavelengths, without regard to the state of polarization of the incident or absorbed light. Absorption in this case is proportional to the number of molecules of analyte present in the test sample.

The term "fluorescence spectrophotometry" as used herein means detection and quantitation of analytes in a test sample by measuring the intensity of light emitted by the analytes at various wavelengths, following their irradiation by incident light at different wavelengths. Fluorescence is proportional to the number of molecules of analyte in the irradiated sample.

The term "first derivative spectrophotometry" as used herein describes the spectrum that is obtained by calculating the rate of change of absorbance with wavelength plotted against wavelength. The term "second derivative spectrophotometry" as used herein describes the spectrum obtained by calculating the rate of change of the first derivative with wavelength plotted against wavelength.

The term "spectrophotometrically active" or "spectrophotometric activity" as used herein refers to a property or characteristic that is detectable by spectrophotometric methods such as absorption spectrophotometry, circular dichroism, fluorescence spectrophotometry, derivative absorption spectrophotometry and the like.

METHODS

Direct Detection of Cholesterol Fractions Using CD Absorption, Spectrophotometric Absorption Detection, or Fluorescence or Derivative Absorption Spectrophotometric Methods In a first embodiment, the present invention is directed to the introduction of a color reaction described in the literature, Cox and Spencer, *Can. J. Chem.,* 29, 217 (1951), as the Chugaev reaction.

The reagents utilized in making the Chugaev reaction are for example 20% w/v $ZnCl_2$ in glacial acetic acid, and 98% acetyl chloride. These materials can be stored in separate containers and will remain usable for many weeks, even when stored at about 40° C. Moreover, the degree of their dryness does not have to be carefully controlled. The product of the Chugaev reaction with cholesterol is reddish orange in color and is thought to be a conjugated triene CD-active derivative of cholesterol. The intensity of the color is a direct measure of the cholesterol concentration. In contrast, dyes used in the known methods for cholesterol analysis are secondary products of cholesterol oxidation and are not derivatives of the cholesterol molecule itself. They are thus an indirect measure of the number of cholesterol molecules present in the test sample.

If desired, the components of the Chugaev reagent may also be stored together in a ratio over the range of about a 1:1 to 4:1 $ZnCl_2$/glacial acetic acid to 98% acetyl chloride, all of which gave satisfactory reactions with cholesterol. Reagents must be kept when stored under airtight conditions in an amber glass, teflon or a similar container. In this regard, an extended period of stability was observed for reactants stored together at 40° C. in amber bottles for at least 4 weeks.

It was observed that when ratios of 1:1 to 4:1 of zinc reagent to acetyl chloride are utilized, voluminous precipitates can occur, which cannot always be removed in a centrifugation step that follows the incubation period. While this is not a serious problem in CD detection, because the difference in absorption of two beams is measured which effectively cancels out the contribution from light scattering, it can be serious when a single beam absorption detection method is used (e.g., absorption detection, fluorescence or derivative absorption spectrophotometry). In this respect, the invention has discovered that when the acetyl chloride is used in an amount in excess of the zinc reagent (e.g., 20%–25% w/v $ZnCl_2$ in glacial acetic acid) problems with precipitates are minimized. Most preferably the acetyl chloride is used in a high relative amount to the zinc reagent. Such preferred ratios range from about 4:1 to 100:1. Alternatively, zinc acetate may be added directly to the acetyl chloride, e.g., 0.95 mg zinc acetate dihydrate in 1.0 ml acetyl chloride.

In a second embodiment, the present invention is directed to a method for forming a spectrophotometrically active product of cholesterol which comprises contacting cholesterol with an acyl compound and a perchlorate effective to form a spectrophotometrically active product of cholesterol.

Perchlorates particularly useful in this embodiment of the present invention are those which are effective to form a spectrophotometrically active product, such as a colored product, with cholesterol. Such perchlorates include but are not limited to those which contain zinc and/or barium, such as zinc perchlorate or barium perchlorate, and including hydrated forms of these; perchloric acid, which for purposes of convenience in the present specification is referred to as a perchlorate, may also be used, as may mixtures of the above. A preferred perchlorate is zinc perchlorate, such as zinc perchlorate hydrate; most especially zinc perchlorate hexahydrate.

Acyl compounds particularly useful in this embodiment of the present invention are those which, in conjunction with the above-defined perchlorates, are effective to form a spectrophotometrically active product, such as a colored product, with cholesterol. An acyl compound useful in this regard has the formula

wherein $R^1$ is halogen, and R is lower alkyl, aryl, alkaryl, aralkyl or mixtures thereof.

As employed herein, the lower alkyl groups contain up to 6 carbon atoms which may be in the normal or branched configuration, including methyl, ethyl, propyl, isopropyl, butyl, isobutyl, t-butyl, amyl, penty, hexyl and the like. Preferred lower alkyl groups contain 1 to 3 carbon atoms; methyl is especially preferred.

The aryl groups are aromatic rings containing from 6 to 14 carbon atoms. Examples of aryl groups include phenyl, α-naphthyl and β-naphthyl.

The alkaryl groups contain up to 16 carbon atoms with each alkyl group containing up to 6 carbon atoms which may be in the normal or branched configuration, and each aryl group containing from 6 to 10 carbon atoms. Preferably, each alkyl group contains 1 to 3 carbon atoms.

The aralkyl groups contain up to 16 carbon atoms with each aryl group containing from 6 to 10 carbon atoms and each alkyl group containing up to 6 carbon atoms which may be in the normal or branched configuration. Preferably, each aryl group contains 6 carbon atoms and each alkyl group contains 1 to 3 carbon atoms.

The halogens include fluorine, chlorine, bromine and iodine. The preferred halogen is chlorine.

In a preferred practice, $R^1$ is halogen, R is lower alkyl, aryl or mixtures thereof. In a particularly preferred practice, $R^1$ is chlorine and R is methyl, resulting in acetyl chloride; or phenyl, resulting in benzoyl chloride, which as those in the art will appreciate manifests a certain toxicity. Acetyl chloride is the most preferred acyl compound.

While the concentration of perchlorate and acyl compound may vary within wide ranges as determinable by those of skill in the art, it is preferred if about 0.3 to 0.7 molar perchlorate is present in about 90 to 100% acyl compound; more preferably about 0.5 to 0.6 molar perchlorate in about 95 to 99% acyl compound; most preferably about 0.5 molar in about 98% acyl compound. This last concentration is especially preferred when zinc perchlorate hexahydrate and acetyl chloride are employed.

In one aspect, the present invention is directed to a method for determining the amount of cholesterol present in a test sample. The cholesterol in the test sample is contacted with the aforedescribed acyl compound and perchlorate effective to form a spectrophotometrically active product with the cholesterol under conditions effective to form said product; the spectrophotometric activity of the product is then evaluated to determine the amount of cholesterol present in the sample. The spectrophotometrically active product in this regard is capable of detection by conventional techniques, such as absorption spectrophotometry, circular dichroism, fluorescence spectrophotometry or derivative absorption spectrophotometry.

In practicing the present invention, the direct, simultaneous, quantitative determination of total cholesterol and its distribution among HDL-C, LDL-C and VLDL-C subfraction in a test sample may be obtained. Thus, upon forming the spectrophotometrically active product with cholesterol in accordance with the present invention, the spectrophotometric activity of the product is measured, from which measurement is calculated the amount of HDL-C, LDL-C, VLDL-L and total cholesterol present in the test sample. Importantly, the method can be performed at ambient conditions, e.g., at about room temperature and at about atmospheric pressure, within a short period of time.

In one embodiment, it is preferred that the spectrophotometric activity of the product is measured by spectrophotometric absorption at wavelengths from between about 150 to about 750 nm; more preferably these measurements are made at three or more distinct wavelengths corresponding to the various subfractions among which the major portion of cholesterol is distributed. Although the wavelengths selected may vary as the choices of reagents and conditions are changed, e.g., volume of sample, volume of reagent, incubation temperature, incubation time, the actual values need not be specified since they are readily determinable by those of skill in the art. Generally, when, for example, zinc perchlorate hexahydrate and acetyl chloride are used, adequate wavelengths for the measurement of spectrophotometric absorption are at about 410 nm, about 456 nm and about 518 nm.

From these measurements the amount of HDL-C, LDL-C and VLDL-C can be directly calculated by solving an algorithm which correlates absorption to the amounts of HDL-C, LDL-C and VLDL-C present in the samples from mathematical relations known to the art. Thus, the concentrations of HDL-C, LDL-C and VLDL-C may be calculated by solving an n·n matrix (where for example, n=3) consisting of three linear Beer's Law equations given the sum of absorbances for each fraction as elaborated upon hereinbelow. Alternatively, the algorithm may utilize multivariate regression analysis which may comprise inter alia techniques of principal component analysis, pattern recognition analysis or partial least squares analysis, also as exemplified hereinbelow and commonly available to the art. Importantly, in this aspect of the present invention, TC is determined by the summation of the subfractions.

In practicing the present invention, the rate at which the spectrophotometrically active product is formed may be controlled, i.e., increased or decreased, by the addition of a modifier to the combination.of acyl compound and perchlorate as hereinbefore defined. Modifiers useful to decrease the rate include water, glacial acetic acid, chloroform and like compounds and mixtures thereof. Generally, to decrease the rate, modifier is present at a concentration of greater than about 10% v/v based upon the acyl compound, such as acetyl chloride.

Modifiers useful to increase the rate include FCl, $HClO_4$ and like compounds and mixtures thereof. Generally, to increase the rate modifier is present at a concentration of about 1–2% v/v based upon the acyl compound, such as acetyl chloride.

Another aspect of this particular embodiment of the present invention is directed to a chemical reagent which comprises an acyl compound and a perchlorate effective as hereinbefore defined to form a spectrophotometrically active product with an analyte such as cholesterol or like lipidic material, including, for example, lipoproteins, anabolic steroids or other steroidal products.

A. Direct Method Using CD

An advantage when using CD in the present invention is that CD allows for great specificity and selectivity in determining the amount of the different cholesterol subfractions present in the test sample, i.e., (VLDL-C+LDL-C) and HDL-C. However, a drawback is that the levels of VLDL-C and LDL-C could not be directly separated using CD.

Figure 1:
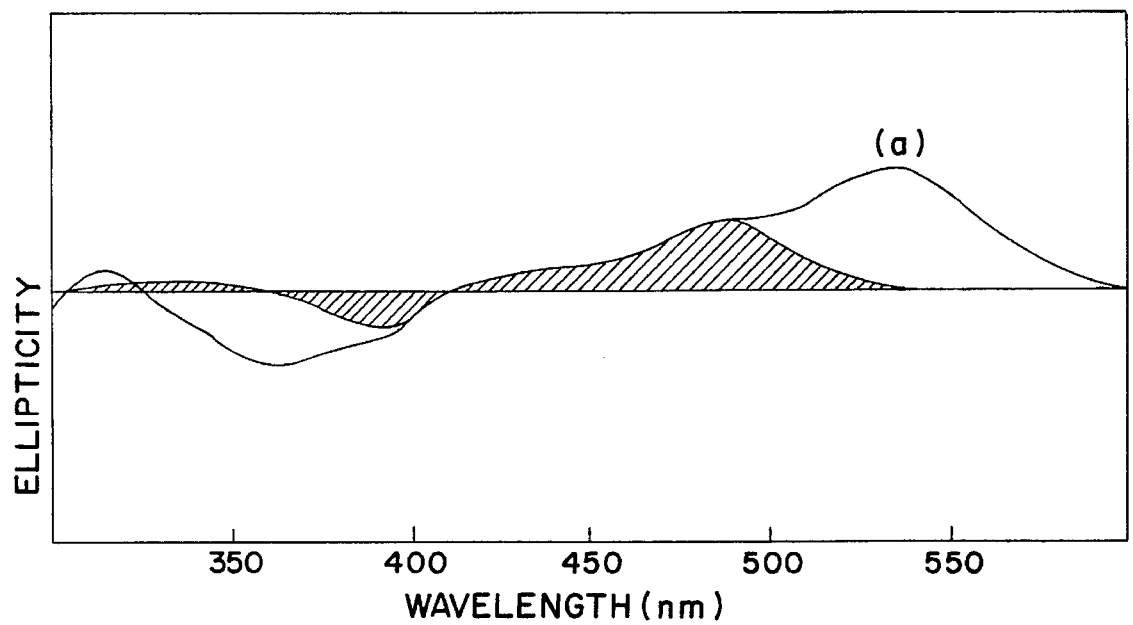
FIG. 1 is a full CD spectrum for the optically active colored product obtained from the reaction of Chugaev reagents with cholesterol. Curve (a) is representative of the total cholesterol, while the shaded area is the spectrum after the addition of the LDL-C, VLDL-C precipitating agent and is therefore representative of the HDL-C fraction only.

The full CD spectrum for the orange colored optically active product from the Chugaev reaction with cholesterol is shown in FIG. 1. The sample is a chloroform solution of the NBS Cholesterol-Standard Reference Material (SRM911a). This spectrum is used as the reference standard for all subsequent serum cholesterol measurements.

In the CD absorption spectrum, the HDL-C and the (VLDL+LDL)-C fractions are associated with different spectral bands and can be measured directly from the same specimen, FIG. 1, without the need for a precipitation step to determine HDL-C. In this regard, measurements at 525 nm give results for the combined (VLDL-C+LDL-C) fractions and measurements at 390 nm (or preferably the algebraic sum of the negative and positive CD absorption peaks at 390 nm and 475 nm, respectively) give results for the HDL-C fraction.

It is thought preferable to determine the algebraic sum of the CD absorption peak heights at about 390 and 574 nm, when determining HDL-C levels, since this method uniformly provides a lower coefficient of variation with respect to the values obtained for HDL-C, versus the method wherein only the CD absorption measurement at about 390 nm is used. The decrease in variation with the formed method results from the fact that the effects of baseline drift are lessened when the algebraic sum of the two peaks is calculated.

In FIG. 1, band assignments were made by comparing the CD spectrum for the total cholesterol, curve (a) in FIG. 1, with the .spectrum for the same sample after the selective precipitation of the low density lipid fractions with phosphotungstate-Mg, i.e., the shaded area in FIG. 1. The 525 nm band maximum was calibrated using NBS cholesterol (SRM 911a). Calibration of the 390 nm maximum was done using secondary HDL-C calibrators supplied by Sigma Chemical Company.

As an example of carrying out one of the methods of the present invention and determining the amounts of cholesterol fractions in a test sample, there is provided Example 1:

EXAMPLE 1

(A) Calibration of the CD instrument: A 50 μl aliquot of a $5\times10^{-3}$M solution of (SRM 911a) cholesterol in AR grade chloroform is placed in a vial of 10 mL total volume. 2.00 mL of the zinc chloride reagent are added and the mixture carefully shaken. 1.00 mL of acetyl chloride is added with care, the mixture shaken, and the vial capped and incubated at 67° C. for 8 minutes. The vial is removed and cooled quickly under water. Chloroform (1.00 mL) is then added to increase the solution volume in the vial. Such an addition of chloroform may be deleted if desired, if the CD analyzer will accommodate a 2.00 mL sample volume, or alternatively, an appropriate solvent substituted therefor. The solution is next transferred to a 1 cm pathlength cuvette and the CD spectrum run from 625 nm–325 nm. The spectrum is corrected on a daily basis for the cell blank and the instrument baseline by subtracting the spectrum for the reagent mixture alone.

(b) Calibration of the CD Spectra: the procedure in (a) is repeated for a number of solution concentrations chosen to coincide with the typical range of serum cholesterol levels in the test sample. From the resultant calibration curve the proportionality constant relating the signal size at 525 nm to the (VLDL LDL)-C level is 1.62 millidegrees per 100 mg/dL. The calibration at 390 nm was done in the same way, but the pure cholesterol was substituted by Sigma HDL-C calibrators. The signal size to HDL-C level at 390 nm is 2.08 millidegrees per 100 mg/dL.

(c) Cholesterol Determination in Clinical Test Samples by CD: the procedure in (a) is repeated for 50 μL aliquots of serum. Before being transferred to the cuvette, the specimen is centrifuged at high speed for 2 minutes. The (VLDL+LDL)-C fraction is calculated from the measured signal height at 525 nm and the HDL-C fraction from the signal height at 390 nm. Their sum give the total cholesterol in the specimen. Selective precipitation of the low density fraction in order to measure the HDL-C fraction is not necessary in routine measurements. It is possible therefore, to do a cholesterol-lipid profile with a volume as little as a finger stick, and get the best precision yet obtained in the measurement of low density lipid fractions.

It should be noted that the reagents can be added in the order indicated in (a) Calibration of the Instrument. However, they can also be added simultaneously as a premixed solution or they can be added in the reverse order, e.g. add the acetyl chloride first, followed by the $ZnCl_2$ reagent. The latter mode of reagent addition had the unexpected effect of reducing the amount of precipitation in the test sample, thereby greatly reducing the scattering of incident light and thereby simplifying the subsequent measurement of absorption either by CD or by conventional spectroscopic absorption. An alternative is to use a reagent comprising zinc acetate (in lieu of zinc chloride in glacial acetic acid) and acetyl chloride.

Figure 2:
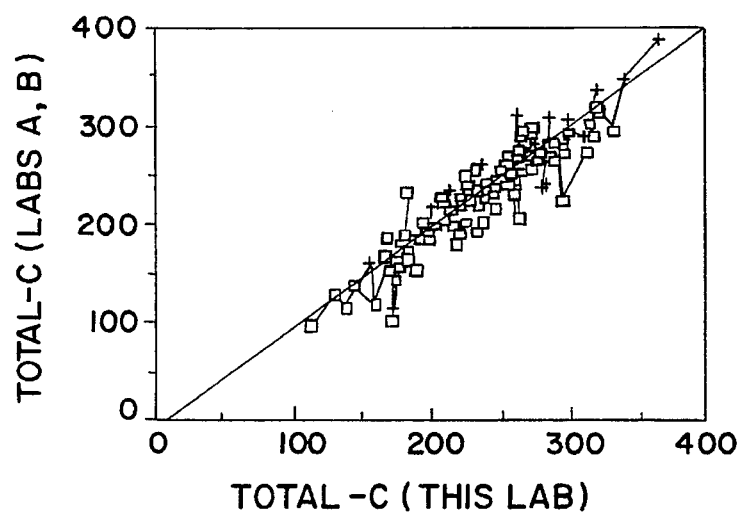
FIG. 2 represents the correlation between TC as measured in serum samples processed by two different labs using prior art processes (Labs A and B), versus total cholesterol as measured by the CD method of the present invention (this lab); y=−10.209+1.0055x, $R^2$=0.835.

(d) Results of Exploratory Work: Cholesterol determinations were made on serum samples provided by two different laboratories, which employ the commercial methods developed by Abbott Laboratories (Lab A) and DuPont (Lab B), respectively. The correlations for total cholesterol levels are excellent, FIG. 2, and well within the limits imposed by the LSP.

Figure 3A:
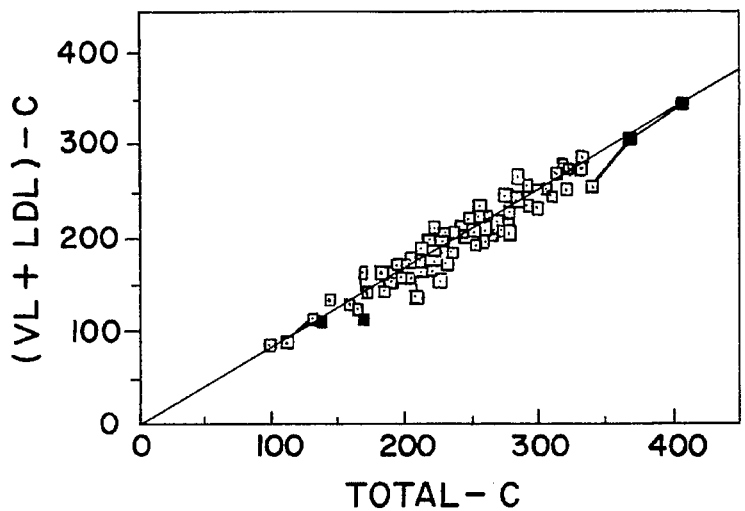
FIG. 3(i a) is a graph of TC vs. (VLDL+LDL)-C using a CD method of the present invention (this lab); y =5.0554+ 0.84693x, $R^2$=0.932.
FIG. 3(b) is a graph of TC vs. (VLDL+LDL)-C using a prior art process (LAB-A); y=−47.672+0.98751x, $R^2$=0.98.
FIG. 3(c) is a graph of TC vs. (VLDL+LDL)-C using a prior art process (LAB-B); y=046.5222+0.9869x, $R^2$=0.98.
Figure 3B:
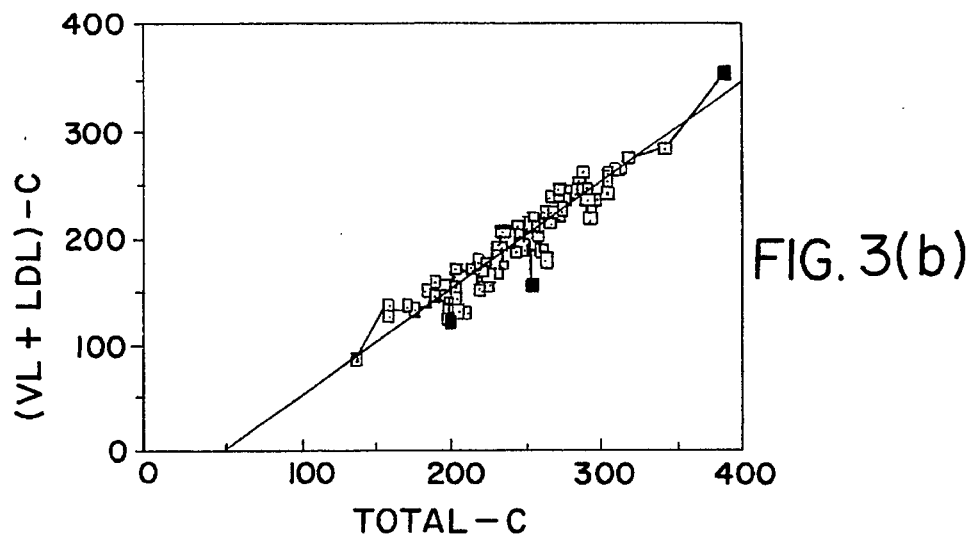
Figure 3C:
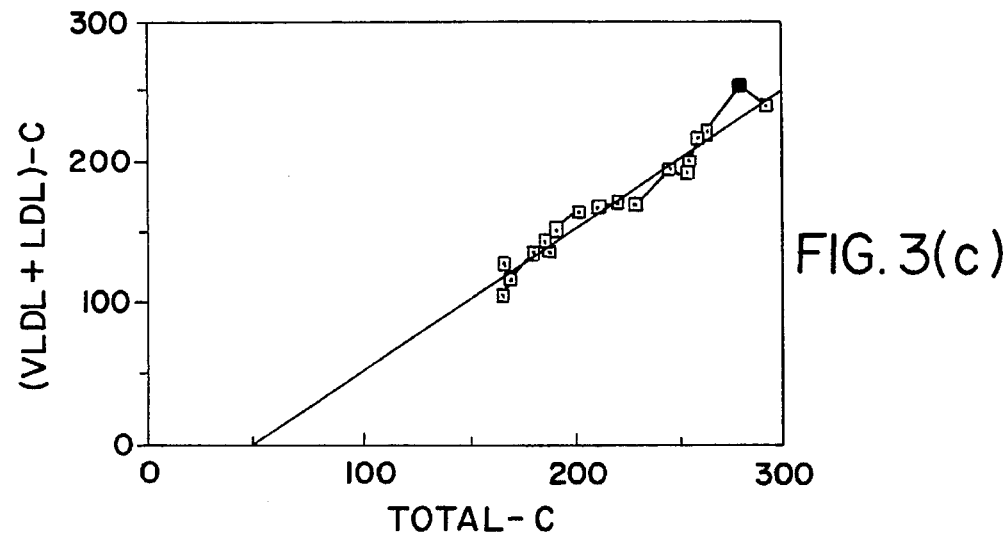
Figure 4A:
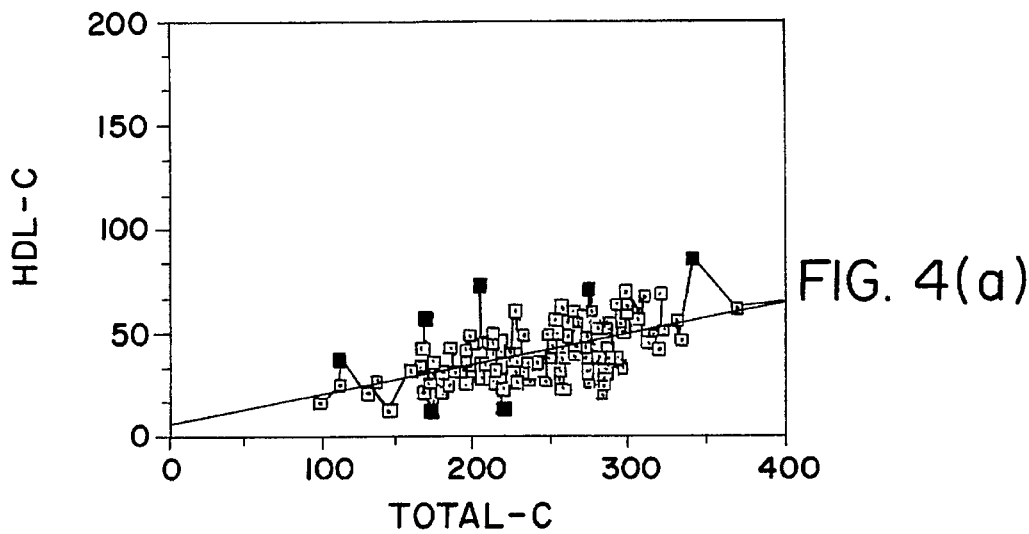
FIG. 4(a) is a graph of TC vs. HDL-C using the CD method of the present invention (this lab); y−5.2861 +0.14995x, $R^2$=0.335.
Figure 4B:
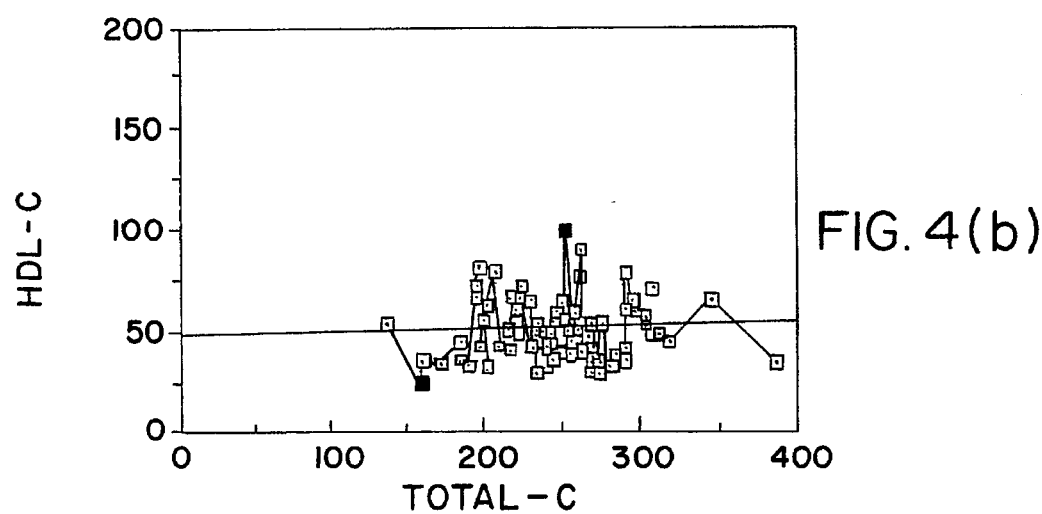
FIG. 4(b) is a graph of TC vs. HDL-C using a prior art process (LAB-A); y 47.648+0.012569x,=$R^2$0.001.
Figure 4C:
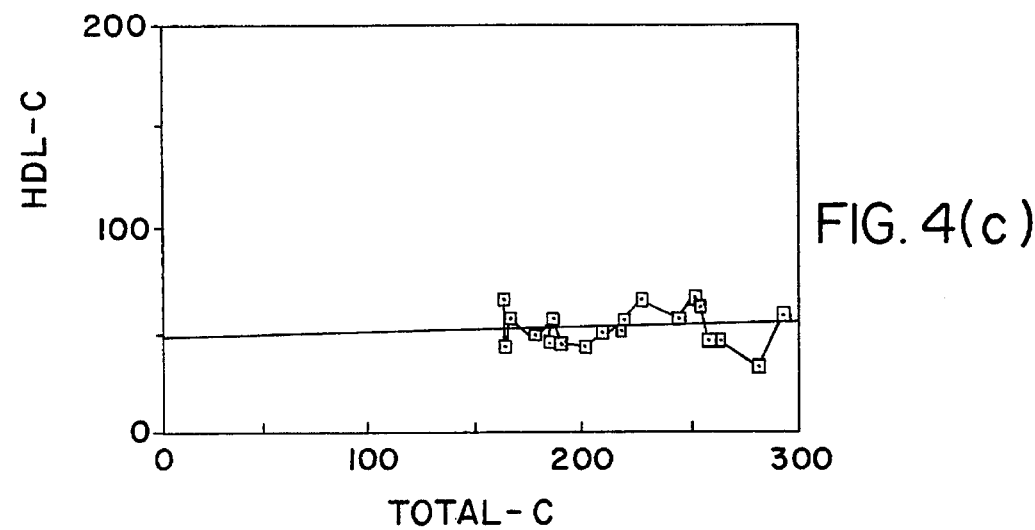
FIG. 4(c) is a graph of TC vs. HDL-C using a prior art process (LAB-B); y=46,522+0.0131x, $R^2$−0.06.

A good case for believing that this new method is an improvement over prior methods, is to compare the correlations for the three data sets treated independently. Plots of total cholesterol versus (VLDL +LDL)-C are linear in every case, but there is a bias of almost 50 mg/dL in the intercepts on the x-axis for both conventional methods (FIGS. 3(b) and 3(c)) and zero correlation between the total and HDL-C data for these same data sets (FIGS. 4(b) and 4(c)). The Chugaev-CD data correlations by comparison, are excellent with low correlation intercepts, FIGS. 3(a) and 4(a), and the correlation slopes indicate that, for these sample populations, the "average" percentages for the HDL-C and (VLDL+LDL)-C fractions are 15% and 85%, respectively, which are in good agreement with the values normally accepted as typical for human serum distributions based upon ultracentrifugation data. Correlation slopes for the previously known spectrophotometric absorption methods are both one, which is not statistically possible, and which arises because the virtually constant measured value of 50 mg/dL for HDL-C is subtracted from measured TC values to obtain the results for (VLDL+LDL)-C.

(e) Accuracy and Analysis Time: Since there are no commercial reference standards for either LDL-C or VLDL-C, the accuracy cannot be evaluated. However, the precision and repeatability in the (VLDL+LDL)-C measurements are better than ±2%. With this level of precision, the confidence in one's ability to correlate the changes in LDL-C in reduction therapy studies, which involved diet and/or exercise modifications, is meaningfully improved.

The approximate time for a single analysis by the Chugaev-CD method with CD detection is about 15 minutes. While this is long compared to the commercial absorption methods used only for TC measurements, results for both low and high density fractions are obtained simultaneously. Because of the stability of the color, the turn around time can be reduced considerably by incubating several samples at once. With greater incident light intensities, sample path lengths can be reduced from 1 cm and the measurements can be automated.

Utilizing Chugaev reagents in procedures such as those provided above, several National Bureau of Standards SRM total cholesterol standards were also examined. The three samples tested were listed in the NBS catalogue as (1951-1) (210.36±2.46 mg/dL total), (1951-2) (242.29±1.83 mg/dL total), and (1951-3) (281.97±1.83 mg/dL total). According to the NBS Certificate of Analysis, the serum was donated by the CDC. The figures in parentheses are those measured at NBS and they compare extremely well with the CDC determinations using the modified Abell-Kendall method. The figures that we obtained from the Chugaev reaction, by adding the CD absorption values for the two fractions (HDL-C and (VLD+LDL)-C) were 206 mg/dL, 241.1 mg/dL, and 286.6 mg/dL, respectively. These results clearly evidence the effectiveness of the present inventive methods in determining cholesterol levels directly and precisely.

In order to further evidence the effectiveness of the present inventive CD methods in determining levels of cholesterol subfractions in a test sample, additional experimental data are provided in Table I.

TABLE I

| | Blood Fractions | | |
|---|---|---|---|
| Patient | VL + LDL(Chug)[1] | HDL(Chug)[2] | HDL(enz)[3] |
| A | 126 | 31 | [63] |
| B | 165 | 28 | [46] |
| C | 220 | 33 | — |
| D | 237 | 34 | [55] |
| E | 199 | 29 | 32 |
| F | 188 | 39 | 36 |
| G | 249 | 36 | 43 |
| H | 199 | 34 | 25 |
| I | 144 | 28 | [53] |
| J | 216 | 46 | 52 |
| K | 190 | 38 | 35 |
| L | 211 | 41 | — |
| M | 239 | 39 | — |
| N | 190 | 39 | [56] |
| O | 220 | 50 | — |
| P | 174 | 46 | 46 |
| Q | 249 | 51 | 57 |
| Q* | 242 | 48 | — |
| R | 184 | 47 | [60] |
| S | 205 | 29 | 33 |
| T | 126 | 46 | 45 |
| U | 157 | 46 | 49 |
| U* | 163 | 41 | — |
| V | 94 | 31 | [86] |
| W | 293 | 38 | — |
| X | 239 | 47 | [84] |
| Y | 207 | 57 | 55 |
| Sigma 400 | 340 | 51 | — |
| Sigma H | 230 | 52 | — |

[1]VL + LDL(Chug) - Cholesterol subfraction VLDL-C + LDL-C using Chugaev reagents and taking CD absorption measurement at 575 nm.
[2]HDL(Chug) - Cholesterol subfraction HDL-C obtained using Chugaev reagents and taking algebraic sum of Cd absorption measurements at 390 and 574 nm.
[3]HDL(enz) - subfraction HDL-C obtained using the enzymatic method designated by Lab(A) and Lab(B).
*Asterisk indicates test was performed on patient's serum using mixed Chugaev reagents stored 4 week at 40° C.
[ ] Brackets indicate HDL measurements which are substantially different from HDL measurements using other methods.

Of the experimental results shown in Table I, it is noted that 12 out of 20 values for each of the HDL-C(Chug) and HDL-C(enz) methods agree to within 10 mg/dL. Such results clearly help to evidence the accuracy of the present methods.

B. Direct Detection Using Spectrophotometric Absorption Detection

The visible absorption spectrum for the colored product of the Chugaev reaction with cholesterol or serum cholesterol shows a strong maximum around 518 nm, a minimum around 460 nm, with shoulders at wavelengths between 460 nm and 365 nm showing a fairly weak absorption maximum (FIG. 6). Additionally, the Chugaev reagent itself absorbs in the visible range and has a weak maximum in the 350–370 nm regions.

In order to ascertain the effectiveness of the present inventive spectrophotometric absorption detection methods, samples of separated HDL-C, VLDL-C, and LDL-C lipoprotein fractions were obtained from Sigma Chemical Company (Sigma; fractions separated by ultrafiltration) and from Oklahoma Medical Research Foundation (OMRF; subfractions separated by ultra-centrifugation). The three subfractions were reacted separately with Chugaev reagents to give colored products which possess different absorption spectra in the visible range. Spectral correspondences between the fractions from the two different sources were excellent for the HDL-C and LDL-C samples. Correspondence for the VLDL-C subfractions were also good. The spectral differences between each of the subfractions is sufficient to enable the three cholesterol subfractions to be qualitatively determined simultaneously in a single experiment without resorting to a selective precipitation step. For purposes of this example, absorption measurements are taken at 518, 450 and 420 nm. The serum spectrum of any test sample is an aggregate of the weighted contribution from each subfraction.

The ability to calculate the amount of each cholesterol subfraction present in a test sample, is due to the inventors' initial postulation that all three subfractions absorb at every wavelength analyzed, so that the general equation for total absorbance $A_T$ of a serum test sample is given by the equation:

$$E_{HDL}[HDL]+E_{VLDL}[VLDL]+E_{LDL}[LDL]=A_T$$

In the above equation, the E coefficients denote the absorbances for each of the subscripted fractions normalized in appropriate units of absorbance/(mg/dL), and the concentration terms [ ] are in mg/dL. Utilizing the above equation, and making the further assumption that each subfraction has the same or a substantially similar absorption coefficient at 518 nm but, as exemplified by the different spectra, have different absorption coefficients at the other wavelengths (in this case 420 and 450 nm), it is possible to calculate the amount of each subfraction present in a test sample by taking an $A_T$ measurement at each of the three discrete wavelengths in the spectrum and solving the resulting 3·3 matrix equation. In order to do this, the individual values for the subscripted E coefficients have to be determined for the three wavelengths selected. Relative values for the E coefficients at different wavelengths were easily obtained within the spectrum of any one of the subfractions. Relating these to the values of the equivalent wavelengths for the other fractions was more difficult, but was achieved and is disclosed herein. In this respect, spectral analysis of about 90 serum samples showed that a direct linear correlation existed between the $A_T$ values measured at 518 nm and the value for total cholesterol (TC) measured in a completely independent study that utilized a conventional method (data from Roche Biomedical). Based on this linear correlation, the inventor presupposed that a normalized value expressed as $A_T/TC$ should be constant from sample to sample.

In order to correlate E values between the spectra for the different subfractions, the inventor postulated that the $A_T/TC$ (or E) values at 518 nm are the same for all three subfractions, as noted above, and that the remaining six E coefficients for the three subfractions can be calculated for the remaining two wavelengths using simple proportions (e.g., $$E_{LDL(420)}=A_{T(420)}/A_{T(518)} \times E_{LDL(518)}.$$

The amount of the above three lipofractions calculated from 60 serum samples utilizing the above technique and 3·3 matrixes provided results in excellent agreement with numbers obtained for the same test samples utilizing a conventional reaction procedure.

The specific test procedure utilized with the 60 samples that gave excellent agreement was as follows. After reagents were added the mixtures were allowed to incubate for 8 minutes at 67° C., thereafter cooled in a waterbath, centrifuged, transferred to a one cm cuvette, and a conventional absorption spectrum run from 700 nm–400 nm. Absorption measurements were taken at 518, 450 and 420 nm, after appropriate corrections for the cell blank and the instrument base line were made. It is not necessary to run the entire spectrum, since absorbance measurements are only needed at the prescribed wavelengths. The nine E values for the wavelengths 518, 450 and 420 nm, respectively, obtained under the above described particular experimental conditions in units of absorbance, dL/gram were as follows: 3.05, 1.97 and 2.52 for HDL-C; 3.05, 1.35 and 2.41 for VLDL-C; and 3.05, 1.31 and 1.34 for LDL-C.

With Chugaev reagents problems may arise in the use of absorption spectrophotometry which do not exist when CD methods are used. Specifically, whenever an absorption detection spectrophotometric method is utilized with Chugaev reagents precipitation may create problems. In order to fully minimize such problems, the Chugaev reagent should be modified such that either the ratio of acetyl chloride to zinc reagent is from 100:1 to 4:1 or zinc acetate is substituted for zinc chloride/acetic acid. The final zinc concentration should be between 0.03 and 0.22 molar. This is a composition much different from the reagent described in the literature.

It is noted that excellent absorption spectra have been obtained for volumes of serum as little as 2 μL. Likewise, excellent spectra were obtained for various acetyl chloride to serum ratios over the general broad range of 100:1 to 20:1 at constant zinc concentrations, and for acetyl chloride to zinc reagent ratios from 100:1 to 4:1 at constant serum amounts. Measurements have also been made with test samples, wherein the total reaction volume was as little as 0.15 mL and in cuvettes having a pathlength as short as 1 mm. Moreover, incubation times as little as two minutes have been achieved with the smaller total volumes, and it is fully envisioned that under conditions where serum concentrations are relatively high, that lower incubation temperature may be utilized. Furthermore, with appropriate miniaturization, centrifugation may be eliminated.

In addition to the Chugaev reagent system described above, it is noted that ACS reagent grade zinc acetate dihydrate readily dissolves in acetyl chloride to a concentration that is similar to the final zinc ion concentration when added as the chloride in glacial acetic acid. Zinc acetate in acetyl chloride therefore can work, if desired, as a single reagent system. For example, if one mL of such a reagent system is added to 10 L of a test serum, there is obtained a reddish-orange product after the usual incubation conditions. The maxima and minima in the spectra are at the same wavelengths but the ratios of the heights of these bands are different from those seen with the zinc chloride reagents with the unexpected finding of a greater difference between the absorbances at 420 and 450 nm. Consequently, new E coefficients would need to be calculated for a 3·3 matrix if the zinc acetate were used rather than zinc chloride in acetic acid. The greater difference at those wavelengths means better precision in the values obtained for the subfractions. Indeed, the coefficients are highly dependent on the composition of the reagent and must be recalculated if the amounts of any of the reagent components are changed. However, such a calculation is in line with those earlier described, and clearly within the skill of those of ordinary skill in the art, based on the present disclosure.

A broad range of alternative reaction conditions to those reaction conditions discussed above, will produce reddish-orange colored products which have spectra that are similar, but not always equivalent to the absorbance spectrum of the species produced under the exact conditions utilized herein (as described above). Even so, when those skilled in the art utilize such alternative reaction conditions in combination with the 3·3 matrix strategy provided herein, and calculate the amounts of each subfraction present, they are practicing the inventor's presently disclosed methods. This is true, even though the nine E coefficients utilized may have to be revised after a recalibration of the spectra for standards of each of the subfractions (e.g., Sigma or OMRF provided subfractions) based on the exact reaction conditions employed. As such, it is envisioned that the present spectrophotometric methods clearly cover all such possible reagent mixtures and reagent ratios, so long as a colored reaction product is formed with the cholesterol subfractions, and the amounts of each subfraction are then determined in a manner as described above.

The above-described spectrophotometric absorption methods offer an opportunity for simultaneous, on-line detection of cholesterol and cholesterol subfractions in clinical samples. The use of spectrophotometric absorption methods in accordance with the present invention also permits much greater sensitivity than the CD methods herein disclosed allow for, since only a very small portion of the incident light can be used for CD signal generation. As such, the spectrophotometric absorption methods herein disclosed also permit the use of smaller volumes of sample, thereby reducing possible interferences caused by other materials and the total amount of precipitates formed by the reaction. Conversely, however, these reactions are more susceptible than CD to interferences from pigments released by hemolysis of the blood samples. Finally, it is important to note that, as with the CD studies mentioned above, addition of the acetyl chloride to the sample first, followed by addition to the $ZnCl_2$/acetic acid reagents reduces even further the interferences caused by precipitation in a clinical sample. Indeed it is possible to carry out spectrophotometric absorbance reactions in the present inventive methods using whole blood samples.

In the following Table II, there is provided comparative data obtained with test samples using both the spectrophotometric absorption/Chugaev method disclosed herein and an enzymatic method for the cholesterol subfractions shown. As may be seen upon review of Table II, excellent results were obtained using the Chugaev reagents/spectrophotometric absorption method herein described (as verified by comparing with results obtained on the same test samples using the enzymatic method).

TABLE II

Subfractions from Enzymatic and Chugaev Methods

| Test Subject | Test | VLDL-C | LDL-C | HDL-C | TC |
|---|---|---|---|---|---|
| 1 | enzymatic | 32 | 155 | 28 | 216 |
|   | Chugaev | 29 | 155 | 35 | 222 |
| 2 | enzymatic | 46 | 178 | 37 | 262 |
|   | Chugaev | 50 | 173 | 42 | 264 |
| 3 | enzymatic | 37 | 110 | 36 | 183 |
|   | Chugaev | 48 | 103 | 31 | 182 |
| 4 | enzymatic | 34 | 133 | 46 | 214 |
|   | Chugaev | 38 | 139 | 36 | 213 |
| 5 | enzymatic | 42 | 155 | 45 | 242 |
|   | Chugaev | 44 | 161 | 41 | 246 |
| 6 | enzymatic | 62 | 113 | 26 | 202 |
|   | Chugaev | 65 | 101 | 35 | 203 |

Based on the above considerations, there is provided herein a novel spectrophotometric absorption detection method, wherein cholesterol subfractions in clinical samples are reacted with either Chugaev reagents or the acyl compound and perchlorate reagent system as defined hereinabove, so that a direct measurement of the cholesterol subfractions can be made. The measurements can be made either as a full spectrum over the range of about 150–700 nm or at 3 selected wavelengths, in this case about 420 nm, 450 nm and 518 nm.

The major procedural difference between the absorption and the CD method relates to the standards used. While cholesterol itself can be used as a standard for the CD reactions, clinical standards for TC and cholesterol subfractions obtained from the CDC, CAP or a commercial source must be used to calibrate the absorption spectrometer.

Further to the above disclosed spectrophotometric methods, given the availability of "pure" samples of VLDL-C, LDL-C and HDL-C, a mathematical algorithm can be prepared, if so desired, which enables one to add the individual subfractions' spectrophotometric absorption spectra in a weighted fashion for each subfraction. In such a manner the total absorption spectrum for the test sample is obtained. Utilizing such a method would be analogous to measuring the spectrophotometric absorption of a colored reaction product at an infinite number of points, instead of just at three or more distinct points as described above.

As an example of practicing the material of the present invention whereby a spectrophotometrically active product of cholesterol in a test sample is formed by contact with an acyl compound and a perchlorate as hereinbefore defined, Example 2 is provided.

EXAMPLE 2

Experimental Conditions:

The reagent consisted of an 0.5M solution of zinc perchlorate six hydrate $[Zn(ClO_4)_2 \cdot 6H_2O]$ in 98% acetyl chloride. After mixing, the solution was centrifuged to remove suspended materials, most probably undissolved ZnO, which is reported by the manufacturer to be a possible impurity. The reagent was stable when stored in a tightly sealed amber-glass container.

A 20 μL aliquot of serum was placed in a glass or polypropylene vial and 2 mL of reagent was carefully added and the mixture was shaken thoroughly. Transfer proteins were precipitated on the addition of the reagent and were quickly and easily removed either by centrifugation or filtration. The supernate was transferred to a sealed, 1 cm pathlength, spectrophotometric cuvette and allowed to stand at room temperature for 15 minutes at which time the absorption spectrum was measured from 750–380 nm. The instrument used was a diode array spectrophotometer, but the necessary data for the lipid profile analysis was obtained using only four wavelengths, one of which (700 nm) was used for the sample baseline correction. The other wavelengths were 410 nm, 456 nm and 518 nm.

The values for total cholesterol in a sample was determined from the absorbance measured at the major maximum, which under the above experimental conditions occurred at 518 nm. The constant that allowed total cholesterol to be calculated was obtained from the slope of the linear correlation between measured absorbance $A_T$ (518) and the total cholesterol measured by the commercially available enzymatic method. The mathematical procedure to calculate the concentration of the three major fractions, VLDL-C, LDL-C and HDL-C was the same as hereinbefore described, i.e., by solving the 3×3 matrix that consists of three linear Beer's Law equations given by the sum of the absorbance for each fraction:

$$A_{T(i)} = A_{VLDL\text{-}C(i)} + A_{LDL\text{-}C(i)} + A_{HDL\text{-}C(i)}$$

wherein i=1–3.

Each A term for a fraction consisted of a product of the concentration of the fraction times a coefficient E: e.g., $A_{LDL\text{-}C(i)} = E_{LDL\text{-}c(1)} \cdot [LDL\text{-}C]$. E Values are usually defined as molar absorbances but for this application the units were converted to mg/dL which is standard for reporting lipid data. The solution required that the nine E coefficients (one for each fraction at three wavelengths) be determined. This could not be done exactly because there are no known samples of reference standards available for the lipid fractions. Therefore, they were arrived at empirically. This was done by comparing lipid panels for a large pool of serum samples that had been measured by the commercially available enzymatic method and by the method of the present invention. The coefficients were systematically adjusted as the size of the pool was enlarged to give the best statistical fit among data for all the fractions.

The results for the lipid profile analysis is presented below in Table III. Enzymatic refers to the independent results measured by Roche Biomedical, Kansas City; spectrophotometric refers to the results from the Chugaev reaction described herein; and kinetic refers to the results from the use of zinc perchlorate hexahydrate and acetyl chloride.

TABLE III

Comparisons of Lipid Panels by Three Methods

| A | B | C | D | E |
|---|---|---|---|---|
| Method | Total | VLDL | LDL | HDL |
| Sample 1 | | | | |
| enzymatic | 160 | 20 | 100 | 40 |
| spectrophotometric | 170 | 25 | 100 | 45 |
| kinetic | 150 | 12 | 90 | 48 |
| Sample 2 | | | | |
| enzymatic | 179 | 13 | 124 | 41 |
| spectrophotometric | 181 | 13 | 121 | 47 |
| kinetic | 165 | 5 | 113 | 47 |
| Sample 3 | | | | |
| enzymatic | 215 | 39 | 141 | 35 |
| spectrophotometric | 229 | 36 | 131 | 62 |
| kinetic | 208 | 23 | 126 | 58 |
| Sample 4 | | | | |
| enzymatic | 204 | 26 | 141 | 36 |
| spectrophotometric | 213 | 24 | 132 | 57 |
| kinetic | 195 | 20 | 125 | 49 |
| Sample 5 | | | | |
| enzymatic | 195 | 68 | 98 | 28 |
| spectrophotometric | 217 | 52 | 106 | 59 |
| kinetic | 202 | 46 | 104 | 52 |
| Sample 6 | | | | |
| enzymatic | 196 | 26 | 129 | 41 |
| spectrophotometric | 200 | 20 | 131 | 49 |
| kinetic | 198 | 23 | 126 | 49 |
| Sample 7 | | | | |
| enzymatic | 233 | 39 | 151 | 42 |
| spectrophotometric | 243 | 28 | 153 | 62 |
| kinetic | 229 | 28 | 148 | 54 |
| Sample 8 | | | | |
| enzymatic | 132 | 36 | 65 | 31 |
| spectrophotometric | 135 | 36 | 60 | 39 |
| kinetic | 119 | 27 | 61 | 30 |
| Sample 9 | | | | |
| enzymatic | 232 | 19 | 160 | 50 |
| spectrophotometric | 231 | 15 | 156 | 60 |
| kinetic | 231 | 18 | 164 | 49 |
| Sample 10 | | | | |
| enzymatic | 168 | 14 | 109 | 44 |
| spectrophotometric | 177 | 21 | 108 | 48 |
| kinetic | 153 | 20 | 100 | 34 |
| Sample 11 | | | | |
| enzymatic | 170 | 46 | 95 | 28 |
| spectrophotometric | 184 | 56 | 85 | 43 |
| kinetic | 178 | 32 | 100 | 45 |
| Sample 12 | | | | |
| enzymatic | 186 | 10 | 113 | 62 |
| spectrophotometric | 193 | 21 | 119 | 53 |
| kinetic | 170 | 10 | 108 | 50 |
| Sample 13 | | | | |
| enzymatic | 201 | 30 | 111 | 59 |
| spectrophotometric | 215 | 49 | 104 | 62 |
| kinetic | 208 | 24 | 120 | 58 |
| Sample 14 | | | | |
| enzymatic | 180 | 26 | 113 | 40 |
| spectrophotometric | 186 | 36 | 97 | 53 |
| kinetic | 186 | 24 | 116 | 46 |
| Sample 15 | | | | |
| enzymatic | 186 | 17 | 127 | 41 |
| spectrophotometric | 194 | 28 | 111 | 55 |
| kinetic | 182 | 21 | 120 | 44 |
| Sample 16 | | | | |
| enzymatic | 175 | 15 | 106 | 54 |
| spectrophotometric | 186 | 26 | 111 | 49 |
| kinetic | 180 | 24 | 119 | 37 |
| Sample 17 | | | | |

TABLE III-continued

Comparisons of Lipid Panels by Three Methods

| A | | B | C | D | E |
|---|---|---|---|---|---|
| 88 | enzymatic | 173 | 9 | 113 | 50 |
| 89 | spectrophotometric | 172 | 22 | 102 | 48 |
| 90 | kinetic | 176 | 18 | 118 | 39 |

EXAMPLE 3

In this example, zinc perchlorate hexahydrate and acetyl chloride were contacted with cholesterol in a test sample following substantially the procedure described in Example 2; however, the calculation of cholesterol in this example was by way of multivariate regression analysis instead of a 3×3 matrix used in Example 2.

Incubation was performed for 15 minutes at ambient temperature. Protein that precipitated on addition of a 2 mL aliquot of zinc perchlorate hexahydrate/acetylchloride reagent to 20 μL of serum was removed by centrifugation or by filtration. The batching of samples reduced the time per test to approximately 5 minutes.

Absorbance Measurements: Full spectral (350–750 nm) absorbance data for a sample with a pathlength of 1 cm were collected on a Hewlett Packard 8452A diode array spectrophotometer; accumulation time was 5 seconds. With the speed and convenience of diode array detection technology, the wavelength range was wider than that used for the method employing Chugaev reagents.

Computational: Since pure forms of cholesterol lipid fractions are not available, neither are the spectra for the individual products of the color reaction. Therefore a mathematical model was developed to resolve the whole spectrum into the contributions from the parts.

(a) 3×3 Matrix Solution: In Example 2, absorbances, $A_{(i)}$, were measured at three principal wavelengths and the lipid profiles were calculated by solving a set of three simultaneous equations of the form:

$$A_{(i)} = E_{VLDL(i)}[VLDL]d + E_{LDL(i)}[LDL]d + E_{HDL(i)}[HDL]d$$

where d was the sample pathlength. The nine E coefficients were evaluated in an empirical manner.

(b) Multivariate Regression Analysis (MVRA): Lipid profile and TC results in this example were determined using MVRA techniques to interpret the full absorbance spectrum, which eliminated simplifying assumptions and investigator bias. The MVRA algorithms that were applied were Partial Least Squares 2 (PLS2) and Principal Component Analysis (PCA) using software for spectroscopic analysis available in the commercial package UNSCRAMBLER II (CAMO A/S, Trondheim, Norway). Spectral resolution in the spectrophotometer was 2 nm so a full spectrum consisted of 200 data points, which represented an enormous increase in the number of degrees of freedom compared to the simpler analysis of Example 2.

Training Set: An analytical model was prepared by compiling a training set that consisted of 35 serum samples for which the lipid profiles had been measured by commercially available enzymatic techniques; VLDL-C here was taken to be 0.2×TG and numbers of LDL-C were calculated using the Friedewald formula. Ranges in values were as wide as could be accessed, namely; 8–80 mg/dL for VLDL-C; 85–222 mg/dL for LDL-C; and 20–80 mg/dL for HDL-C. Using both the PLS2 and PCA algorithms, the optimum fit to the spectral data for these 35 samples was obtained using three factors. The percent residual variance that was observed was about 25% with only the first factor and less than 0.05% for all three. No corrections were made for noise or background and no weighting corrections were introduced.

As a test to determine if full spectral analysis was really necessary, the MVRA subroutines were used to identify the optimum wavelengths, i.e., those that are most sensitive to variations in the amounts of each fraction. Alternative models were prepared using reduced data sets limited to 100, 130, 14, 6 and 4 wavelengths respectively. Little difference was seen in the percent residual variance through the model with 6 points, and 4 could be used with little loss in the quality of the fit. For purposes of the present example, absorbances were measured at six wavelengths.

Sample Predictions: The above-described analytical model was used to predict lipid profiles for several hundred samples which were about equally split between regular TG and high TG levels. The major source of full lipid profile data for comparisons between 5 methods was Roche Biomedical, Kansas City, which utilized commercially available enzymatic techniques. The major source for HTG samples was the Stillwater Medical Center. For the latter, only TC and TG levels were reported.

The formation of the spectrophotometrically active product was performed with the HTG samples in precisely the same way and it was assumed that the same model could be extrapolated to include them. Four of the thirty five in the original training set were HTG samples. For these four, TG levels were slightly above 400 mg/dL; HDL values were measured, and lipid profiles calculated.

In this treatment, values for the fractions were determined directly and TC was calculated from their sum. Thus, unlike the enzymatic methods, TC was not measured experimentally.

Absorbance Spectra: A comparison of spectra for the colored products from one regular and two HTG serum samples is shown in FIG. 10. All three had a TC of about 186 mg/dL, as measured enzymatically. The critical part of the spectrum for discrimination among the lipid fractions was in the range of about 360 to about 480 nm.

Training Set: As seen in FIG. 11, very good linear correlations for VLDL-C, LDL-C and TC between methods was obtained for the training set. As seen in FIG. 12, the linear correlation for HDL-C was not nearly as good, but it showed an improvement over the Chugaev-reagent method. The result from a paired t-test suggested that there was a correlation, and further evidence to support such a correlation was given by the shape of the bivariate ellipse which, as shown in FIG. 12, was drawn with a confidence region of 65%, which meant that for a normal distribution in X and Y, 65% would lie within the ellipse.

Predictions:

Regular Samples: As shown in FIG. 13(a), the between-methods linear correlation for TC was excellent. The range was from about 58 to about 500 mg/dL and the figure included data for HTG as well as regular samples. This was significant because TC is measured in one method and calculated in the other, which validated the MVRA models used for the spectral interpretation.

As shown in FIG. 13(b), the between-methods linear correlations were also very strong for the LDL-C fraction, which suggested that the measurement of LDL-C by the direct method of the present invention was reliable. As shown in FIG. 13(c), the correlation of HDL-C was only slightly worse than it was for the training set. The VLDL-C correlation for samples with TG less than about 400 mg/dL was good, as shown in FIG. 14(a).

HTG Samples: Absorbances in the range of about 360 to about 430 nm increased dramatically with increasing TG. It was significant that the increase in the maximum absorbance at 360 nm was non-linear with the amount of TG, as shown in FIG. 10. A linear dependence would only be expected if the band could be assigned entirely to VLDL-C absorption and the approximation VLDL-C=0.2 TG were true for HTG samples, which it was not. Meaningful results for lipid profiles were obtained for HTG samples where the TG level was as high as 2000 mg/dL. Between 400 and 1000 mg/dL, the VLDL-C/TG ratio was seen to decrease from 0.2 to 0.12 which is manifested in the curvature observed in the plots of VLDL-C (spec) vs. TG, as shown in FIG. 14(b). This was consistent with the fact that the Friedewald equation, with VLDL-C=0.2×TG, fails at high TG levels.

An inverse correlation between HDL-C and TG has sometimes been alluded to. As long as the routine measurement of VLDL-C was limited to 0.2×TG and TG values were less than TG=400 mg/dL, the correlation had not been obvious. As shown in FIG. 15, adding VLDL-C data for HTG samples emphasized the relationship.

C. Direct Detection Using Fluorescence and Derivative Absorption Spectrophotometric Methods The products of the reaction of cholesterol with the Chugaev reagents are fluorescent. Moreover, fluorescence spectra for the three lipoprotein subfractions VLDL-C, LDL-C and HDL-C are different from each other and from the spectrum for a serum sample (see FIGS. 7(a), 7(b) and 7(c)). The mathematical analysis of fluorescence data, wherein one calculates the amounts of each of the subfractions present in a serum test sample is entirely equivalent to that described above for the conventional absorbance detection spectrophotometry. All that is required to initiate the calculation are the nine fluorescence coefficients for whatever three wavelengths are selected in the fluorescence spectrum for serum. In this respect, wavelengths different from those utilized in conventional absorption spectrophotometry are needed, since the maximum and minimum wavelengths for fluorescence occur at longer wavelengths.

Similarly, derivative absorption spectrophotometry may also be utilized to calculate the amount of a cholesterol subfraction present in the test serum sample. For example, first and second derivatives of absorbance spectra can be utilized for analytical measurements. Copies of derivative absorbance spectra for each of the three lipoprotein subfractions are shown in FIG. 8. FIG. 8(a) shows the first and second derivative for VLDL-C; FIG. 8(b) shows the first and second derivative for LDL-C; and FIG. 8(c) shows the first and second derivative for HDL-C. In each of FIGS. 8(a)–8(c), the solid line denotes a first derivative to the absorbance spectrum and the dotted line denotes the second derivative of the absorbance spectra. Each of the subfractions utilized to obtain the graphs 8(a)–8(c) were obtained from Sigma Chemical Company. When utilizing derivative absorption spectrophotometry, subtle differences exist between the spectra for each of the fractions. Again, the mathematical analysis is completely analogous to that discussed above for absorbance detection and fluorescence spectrophotometries. However, three new wavelengths would need to be chosen. Signal intensities at the band maxima are much better separated than with other methods and precision may therefore be increased. In two measurements on serum samples (see FIGS. 9(a) and 9(b)) it was determined that the peak to peak heights for the two major bands were directly proportional to TC. Data collection utilizing derivative spectrophotometry requires the use of a full spectrum analysis.

INVENTIVE APPARATUS

Upon review of the above methods section, it can be easily ascertained that the present inventive methods have many advantageous attributes when compared with presently known methods for determining cholesterol levels in test samples. However, the present invention also encompasses novel instruments, which allow those skilled in the art to practice the present inventive methods. Such inventive instruments are outlined above (see Section entitled "Summary of the Invention").

A spectrophotometric instrument encompassed hereby should be equipped with 1 or more spectrophotometric absorption detectors capable of measuring the absorption of the colored products of the Chugaev reagent over a range of from about 360–700 nm, or at discrete points therein such as about 518 nm, 450 nm and 420 nm. If automated, it should also have the capability of adding the reagents to separate sample containers for analysis or to sequentially add the components of the reagents to minimize problems due to precipitation of proteins. Finally, any such absorption spectrophotometer, manual or automatic, should preferably have the means to determine the levels of each subfraction present in a serum test sample by a calculation or computation from the absorption values obtained. Specifically, the instrument should have the ability to compute the results of the 3·3 matrix, with nine pre-programmed constants, to establish the levels of VLDL-C, LDL-C and HDL-C present, and to use these values to compute the TC present in the sample, or alternatively, should be equipped with the ability to employ multivariate regression analysis to establish these levels.

It should be noted that the 3·3 matrix represents the minimum possible to measure the three subfractions. It is possible that finer analysis of the spectrum produced by the reagent will indicate that constants at other specific wavelengths will provide useful information, e.g., about specific molecular entities within the various subfractions. In that case, the instrument should be construed to analyze matrixes larger than 3·3.

EXAMPLE 4

This example describes the use of modifier to control the rate of reaction using acyl compound and perchlorate.

Modification of Reagent to Manage Reaction Rates:

The rate of the color reaction and the reagent using acetyl chloride and zinc perchlorate hexahydrate can be increased or decreased by using a modifier in the following manner:

(a) a rate decrease by a factor of two or more was observed when either water, or glacial acetic acid, or chloroform at a level greater than 10% v/v was added to acetyl chloride. Water must be added with great care because of the heat of mixing. At water levels greater than 20% a blue colored solution was produced due to reaction with protein. At 50% chloroform the reagents were immiscible. The rate was controlled by selecting the appropriate mole fraction for the added solvent. Retardation of the reaction at 25° C. by the addition of any of these solvents can be used to advantage if a temperature of 37° C. is preferred for the reaction.

(b) a rate increase was observed when strong acid (HCl or $HClO_4$) was added in the amount of 1.2% v/v. Again great care must be used when adding the aqueous acids. The spectrum after 10 minutes was the same as that for the unmodified reagent after 15 minutes, but the spectrum for the acid mixture changes considerably over the next 5 five minutes so more careful control of the condition would be necessary.

Zinc perchlorate hexahydrate dissolved easily in acetyl chloride and the reagent has a relatively long shelf life in a sealed container under ambient conditions. The shelf life was extended when the reagent was stored in the refrigerator. With some commercial products a slight amount of insoluble material is left. This was readily removed by slow speed centrifugation and the data for this reagent compared exactly with data where the zinc perchlorate completely dissolved. For measurements at a temperature of 25° C. the procedure called for the thorough mixing of 2 mL of the modified single reagent with a 20–50 μL aliquot of serum, centrifuging (or filtering) the mixture to remove precipitated proteins, and measurement. The visible spectrum of the product changed with time and the reaction was approximately 95–98% complete after 15 minutes at which time the absorbance spectrum was measured from 700–400 nm against a reagent blank. The spectrum for the colored product after 15 minutes is analogous to that observed for the zinc chloride (modified Chugaev) reagent with a slight blue shift in the wavelengths of the minimum and second maximum.

Calculations of TC and its distribution among the three major lipoproteins were done in exactly the same way as before, e.g., a 3×3 matrix of linear Beer's Law equations are set up for three distinct wavelengths, at 518, 456 and 410 nm. Reagent blank and instrument baseline were measured at 700 nm. Absorbance coefficients were determined empirically as before, by first assuming that all three fractions had the same molar absorbance at 518 nm and subsequently ratio-ing respective absorptions at 518 nm. For VLDL-C the current adjusted coefficients are: 2.70, 2.90; for LDLC they are: 2.70, 1.15 and 1.20; and for HDL-C they are: 2.70, 1.25 and 2.30.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for forming a spectrophotometrically active product of cholesterol which comprises contacting cholesterol with an acyl compound having the formula:

wherein $R^1$ is halogen,
R is selected from the group consisting of lower alkyl, aryl, alkaryl and aralkyl;
and a perchlorate effective to form a spectrophotometrically active product of said cholesterol, said perchlorate selected from the group consisting of zinc perchlorate, barium perchlorate and perchloric acid.

2. The method of claim 1 wherein said cholesterol is distributed among HDL-C, LDL-C and VLDL-C subfractions.

3. The method of claim 1 wherein said perchlorate is zinc perchlorate hexahydrate.

4. The method of claim 1 wherein $R^1$ is halogen and R is lower alkyl, aryl or mixtures thereof.

5. The method of claim 4 wherein $R^1$ is chlorine and R is methyl.

6. The method of claim 1 wherein said perchlorate is present in a concentration of about 0.30–0.7 molar in about 90–100% acyl compound.

7. The method of claim 6 wherein said perchlorate is present in a concentration of about 0.40–0.6 molar in a concentration of about 95–99% acyl compound.

8. The method of claim 7 wherein said perchlorate is present in a concentration of about 0.5 molar in about 98% acyl compound.

9. The method of claim 8 wherein said perchlorate is zinc perchlorate hexahydrate and said acyl compound is acetyl chloride.

10. The method of claim 1 wherein said spectrophotometrically active product is a colored product.

11. A method for determining the amount of cholesterol present in a test sample which comprises contacting a test sample in which cholesterol is present with an acyl compound having the formula:

wherein $R^1$ is halogen,
R is selected from the group consisting of lower alkyl, aryl, alkaryl and aralkyl,
and a perchlorate effective to form a spectrophotometrically active product with said cholesterol, said perchlorate selected from the group consisting of zinc perchlorate, barium perchlorate and perchloric acid, and evaluating said spectrophotometric activity to determine the amount of said cholesterol present in said sample.

12. The method of claim 11 wherein said cholesterol is distributed among HDL-C, LDL-C and VLDL-C subfractions.

13. The method of claim 12 wherein said zinc perchlorate is a zinc perchlorate hydrate, $R^1$ is halogen and R is lower alkyl or aryl.

14. The method of claim 13 wherein said perchlorate is zinc perchlorate hexahydrate and said acyl compound is acetyl chloride.

15. The method of claim 1 wherein said perchlorate is present in a concentration of about 0.30–0.7 in about 90–100% acyl compound.

16. The method of claim 15 wherein said perchlorate is present in a concentration of about 0.40–0.6 molar in about 95–99% acyl compound.

17. The method of claim 16 wherein said perchlorate is present in a concentration of about 0.5 molar in about 98% acyl compound.

18. The method of claim 17 wherein said perchlorate is zinc perchlorate hexahydrate and said acyl compound is acetyl chloride.

19. The method of claim 11 wherein said spectrophotometrically active product is capable of detection by circular dichroism, absorption spectrophotometry, fluorescence spectrophotometry or derivative absorption spectrophotometry.

20. The method of claim 11 wherein said spectrophotometric activity is evaluated by measuring the absorption spectrum of said product at wavelengths from between about 150 to about 750 nm.

21. A method for direct, simultaneous, quantitative determination of total cholesterol and its distribution among HDL-C, LDL-C and VLDL-C subfractions in a test sample which comprises contacting a test sample containing cholesterol distributed among HDL-C, LDL-C and VLDL-C subfractions with an acyl compound having the formula:

wherein $R^1$ is halogen,

R is selected from the group consisting of lower alkyl, aryl, alkaryl and aralkyl, and a perchlorate effective to form a spectrophotometrically active product with said cholesterol, said perchlorate selected from the group consisting of zinc perchlorate, barium perchlorate and perchloric acid; measuring the spectrophotometric absorption of said product; and calculating from said absorption measurement the amount of HDLC, LDL-C and VLDL-C and total cholesterol present in said test sample.

22. The method of claim 21 wherein said zinc perchlorate is a zinc perchlorate hydrate, $R^1$ is halogen and R is lower alkyl or aryl.

23. The method of claim 22 wherein said perchlorate is zinc perchlorate hexahydrate and said acyl compound is acetyl chloride.

24. The method of claim 21 wherein said perchlorate is present in a concentration of about 0.30–0.7 molar in about 90–100% acyl compound.

25. The method of claim 24 wherein said perchlorate is present in a concentration of about 0.40–0.6 molar in about 95–99% acyl compound.

26. The method of claim 25 wherein said. perchlorate is present in a concentration of about 0.5 molar in about 98% acyl compound.

27. The method of claim 26 wherein said perchlorate is zinc perchlorate hexahydrate and said acyl compound is acetyl chloride.

28. The method of claim 21 wherein said spectrophotometric absorption of said product is measured at wavelengths from between about 150 to about 750 nm.

29. The method of claim 28 wherein said spectrophotometric absorption of said product is measured at three or more distinct wavelengths from between about 150 to about 750 nm.

30. The method of claim 29 wherein said spectrophotometric absorption of said product is measured at wavelengths of about 410 and about 518 nm.

31. The method of claim 29 wherein the amounts of HDL-C, LDL-C and VLDL-C present in said sample are determined by solving an algorithm which correlates the spectrophotometric absorption of said product to the amounts of HDL-C, LDL-C and VLDL-C present in said test sample.

32. The method of claim 31 wherein the amounts of HDL-C, LDL-C and VLDL-C present in said sample are determined by solving an n·n matrix wherein n is the number of distinct wavelengths at which the spectrophotometric absorption of said product is measured.

33. The method of claim 32 wherein n is three.

34. The method of claim 31 wherein said algorithm involves multivariate regression analysis.

35. The method of claim 34 wherein said multivariate regression analysis comprises principal component analysis, pattern recognition analysis or partial least squares analysis.

36. The method of claim 21 wherein the rate at which said spectrophotometrically active product is formed is controlled by the addition of a modifier to said acyl compound and said perchlorate.

37. The method of claim 36 wherein said rate is decreased and said modifier is selected from the group consisting of water, glacial acetic acid and chloroform.

38. The method of claim 36 wherein said rate is increased and said modifier is selected from the group consisting of HCl and $HClO_4$.

39. The method of claim 37 wherein said modifier is present at a concentration of greater than about 10% v/v based upon said acyl compound.

40. The method of claim 38 wherein said modifier is present at a concentration of about 1–2% v/v based upon said acyl compound.

* * * * *

UNITED STATES PATENT AND TRADEMARK OFFICE
CERTIFICATE OF CORRECTION

PATENT NO. : 5,593,894
DATED : January 14, 1997
INVENTOR(S) : Neill Purdie

It is certified that error appears in the above-identified patent and that said Letters Patent is hereby corrected as shown below:

Column 6, line 12: "(i a)" should read --(a)--
Column 6, line 23: "y 47.648" should read --y=47.648--

Column 6, line 25: "$R^2$-0.06" should read --$R^2$=0.06--
Column 8, line 50: "obtainedby" should read --obtained by--
Column 12, line 23: ".spectrum" should read --spectrum--
Column 12, line 57: "(VLDL LDL)" should read --(VLDL + LDL)--
Column 20, line 49, Table III, line 67: "120" should read --128--
Column 21, line 44: "$E_{VLDL(I)}$" should read --$E_{VLDL(i)}$--

Column 22, line 22: delete "5"
Column 26, line 45, Claim 15: "0.30-0.7 in" should read --0.3-0.7 molar in--
Column 26, line 48, Claim 16: "0.40" should read --0.4--
Column 27, line 26, Claim 24: "0.30" should read --0.3--
Column 27, line 28, Claim 25: "0.40" should read --0.4--
Column 27, line 30, Claim 26: after "said" delete --.--
Column 28, line 5, Claim 30: "410 and about 518 nm" should read --410 nm, about 456 nm and about 518 nm--

Signed and Sealed this

Twenty-third Day of June, 1998

*Attest:*

BRUCE LEHMAN

*Attesting Officer*       *Commissioner of Patents and Trademarks*